United States Patent [19]

Anthony et al.

[11] Patent Number: 5,686,472
[45] Date of Patent: Nov. 11, 1997

[54] INHIBITORS OF FARNESYL-PROTEIN TRANSFERASE

[75] Inventors: Neville J. Anthony, Hatfield; S. Jane deSolms, Norristown; Ta Jyh Lee, deceased, late of Lansdale, all of Pa., by Ling Lin Lee, legal representative

[73] Assignee: Merck & Co., Inc., Rahway, N.J.

[21] Appl. No.: 143,943

[22] Filed: Oct. 27, 1993

Related U.S. Application Data

[63] Continuation-in-part of Ser. No. 968,025, Oct. 29, 1992, abandoned.

[51] Int. Cl.$^6$ .................. C07D 213/28; C07C 381/00; C07C 729/00; A61K 31/41
[52] U.S. Cl. .................. 514/357; 514/362; 514/365; 546/336; 548/338.5; 562/444; 562/445; 562/448; 562/553; 562/556; 562/557; 562/559
[58] Field of Search .................. 562/553, 559, 562/556, 557, 444, 445, 448; 546/336; 548/338.5; 514/357, 365, 362

[56] References Cited

U.S. PATENT DOCUMENTS

| | | | |
|---|---|---|---|
| 5,043,268 | 8/1991 | Stock | 435/15 |
| 5,141,851 | 8/1992 | Brown et al. | 435/15 |
| 5,238,922 | 8/1993 | Graham | 514/18 |
| 5,326,773 | 7/1994 | de Solms | 514/336 |
| 5,340,828 | 8/1994 | Graham | 514/357 |
| 5,352,705 | 10/1994 | Deana | 514/630 |
| 5,504,212 | 4/1996 | de Solms et al. | 546/336 |

FOREIGN PATENT DOCUMENTS 0 456 180 A1  11/1991  European Pat. Off. .
91/16340  10/1991  WIPO .

OTHER PUBLICATIONS

Kohl, N.E. et al., "Protein farnesyltransferase inhibitors block the growth of ras-dependent tumors in nude mice", Proc. Natl. Acad. Sci. USA, vol. 91, pp. 9141–9145 (1994).
Goldstein, J.S., et al. Journal of Biological Chemistry, vol. 266, No. 24 pp. 15575–15578 (1991).

Primary Examiner—C. Warren Ivy
Assistant Examiner—Raymond Covington
Attorney, Agent, or Firm—David A. Muthard; Mark R. Daniel

[57] ABSTRACT

The present invention is directed to compounds which inhibit farnesyl-protein transferase (FTase) and the farnesylation of the oncogene protein Ras. The invention is further directed to chemotherapeutic compositions containing the compounds of this invention and methods for inhibiting farnesyl-protein transferase and the farnesylation of the oncogene protein Ras.

6 Claims, No Drawings

INHIBITORS OF FARNESYL-PROTEIN TRANSFERASE

CROSS REFERENCE

This Application is a Continuation-In-Part application of U.S. Ser. No. 07/968,025 filed on Oct. 29, 1992 abandoned.

BACKGROUND OF THE INVENTION

The Ras gene is found activated in many human cancers, including colorectal carcinoma, exocrine pancreatic carcinoma, and myeloid leukemias. Biological and biochemical studies of Ras action indicate that Ras functions like a G-regulatory protein, since Ras must be localized in the plasma membrane and must bind with GTP in order to transform cells (Gibbs, J. et al., *Microbiol. Rev.* 53:171–286 (1989). Forms of Ras in cancer cells have mutations that distinguish the protein from Ras in normal cells.

At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Aaa is an aliphatic amino acid, the Xaa is any amino acid) (Willumsen et al., *Nature* 310:583–586 (1984)). Other proteins having this motif include the Ras-related GTP-binding proteins such as Rho, fungal mating factors, the nuclear lamins, and the gamma subunit of transducin.

Farnesylation of Ras by the isoprenoid farnesyl pyrophosphate (FPP) occurs in vivo on Cys to form a thioether linkage (Hancock et al., *Cell* 57:1167 (1989); Casey et al., *Proc. Natl. Acad. Sci. USA* 86:8323 (1989)). In addition, Ha-Ras and N-Ras are palmitoylated via formation of a thioester on a Cys residue near a C-terminal Cys farnesyl acceptor (Gutierrez et al., *EMBO J.* 8:1093–1098 (1989); Hancock et al., *Cell* 57:1167–1177 (1989)). Ki-Ras lacks the palmitate acceptor Cys. The last 3 amino acids at the Ras C-terminal end are removed proteolytically, and methyl esterification occurs at the new C-terminus (Hancock et al., ibid). Fungal mating factor and mammalian nuclear lamins undergo identical modification steps (Anderegg et al., *J. Biol. Chem.* 263:18236 (1988); Farnsworth et al., *J. Biol. Chem.* 264:20422 (1989)).

Inhibition of Ras farnesylation in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate-limiting enzyme for the production of polyisoprenoids and the farnesyl pyrophosphate precursor. It has been shown that a farnesyl-protein transferase using farnesyl pyrophosphate as a precursor is responsible for Ras farnesylation. (Reiss et al., *Cell*, 62:81–88 (1990); Schafer et al., *J. Biol. Chem.*, 265:14701–14704 (1990); Schafer et al., *Science*, 249:1133–1139 (1990); Manne et al., *Proc. Natl. Acad. Sci USA*, 87:7541–7545 (1990)).

Inhibition of farnesyl-protein transferase and, thereby, of farnesylation of the Ras protein, blocks the ability of Ras to transform normal cells to cancer cells. The compounds of the invention inhibit Ras farnesylation and, thereby, generate soluble Ras which, as indicated infra, can act as a dominant negative inhibitor of Ras function. While soluble Ras in cancer cells can become a dominant negative inhibitor, soluble Ras in normal cells would not be an inhibitor.

A cytosol-localized (no Cys-Aaa$^1$-Aaa$^2$-Xaa box membrane domain present) and activated (impaired GTPase activity, staying bound to GTP) form of Ras acts as a dominant negative Ras inhibitor of membrane-bound Ras function (Gibbs et al., *Proc. Natl. Acad. Sci. USA* 86:6630–6634(1989)). Cytosollocalized forms of Ras with normal GTPase activity do not act as inhibitors. Gibbs et al., ibid, showed this effect in Xenopus oocytes and in mammalian cells.

Administration of compounds of the invention to block Ras farnesylation not only decreases the amount of Ras in the membrane but also generates a cytosolic pool of Ras. In tumor cells having activated Ras, the cytosolic pool acts as another antagonist of membrane-bound Ras function. In normal cells having normal Ras, the cytosolic pool of Ras does not act as an antagonist. In the absence of complete inhibition of farnesylation, other farnesylated proteins are able to continue with their functions.

Farnesyl-protein transferase activity may be reduced or completely inhibited by adjusting the compound dose. Reduction of farnesyl-protein transferase enzyme activity by adjusting the compound dose would be useful for avoiding possible undesirable side effects resulting from interference with other metabolic processes which utilize the enzyme.

These compounds and their analogs are inhibitors of farnesyl-protein transferase. Farnesyl-protein transferase utilizes farnesyl pyrophosphate to covalently modify the Cys thiol group of the Ras CAAX box with a farnesyl group. Inhibition of farnesyl pyrophosphate biosynthesis by inhibiting HMG-CoA reductase blocks Ras membrane localization in vivo and inhibits Ras function. Inhibition of farnesyl-protein transferase is more specific and is attended by fewer side effects than is the case for a general inhibitor of isoprene biosynthesis.

Previously, it has been demonstrated that tetrapeptides containing cysteine as an amino terminal residue within the CAAX sequence inhibit Ras farnesylation (Schafer et al., ibid; Reiss et. al., ibid; Reiss et al., *PNAS*, 88:732–736 (1991)). Such inhibitors may inhibit while serving as alternate substrates for the Ras farnesyl-transferase enzyme, or may be purely competitive inhibitors (U.S. Pat. No. 5,141,851 University of Texas).

The compounds of the present invention are tetrapeptide-based oxa, thia, oxothia or dioxothia isosteres of the general structure C-[yCH$_2$NH]Xaa$_1$[yCH$_2$T]Xaa$^2$-Xaa$^3$ wherein C is cysteine, Xaa$^{1-3}$ is any amino acid, T is either oxygen or S(O)$_m$ and m is 0, 1 or 2. Reduction of the amide linkages between C and Xaa$^1$ and between Xaa$^1$ and Xaa$^2$, and replacement of the amino group between Xaa$^1$ and Xaa$_2$ by T as shown confers both chemical and metabolic stability to the compounds of this invention and thereby enhances their activity in vivo (cell culture). The noted structural modifications may also lead to an unexpected improvement of enzyme-inhibitory activity. Furthermore, of particular utility is the observation that the lactone or ester forms of these inhibitors are prodrugs that efficiently deliver the active hydroxy acids or acids, respectively, to the intracellular compartment that is the site of Ras farnesylation.

It is, therefore, an object of this invention to develop tetrapeptide-based compounds wherein the first amide linkage is reduced and the second amide linkage is replaced by methyleneoxa, methylenethia, methyleneoxothia or methylenedioxothia linkages, and which will inhibit farnesyl-protein transferase and the farnesylation of the oncogene protein Ras. It is a further object of this invention to develop chemotherapeutic compositions containing the compounds of this invention, and methods for producing the compounds of this invention.

SUMMARY OF THE INVENTION

The present invention includes compounds which are tetrapeptide-based oxa, thia, oxothia and dioxothia isosteres and which inhibit farnesyl-protein transferase and the farnesylation of the oncogene protein Ras, chemotherapeutic compositions containing the compounds of this invention, and methods for producing the compounds of this invention.

The compounds of this invention are illustrated by the formulae:

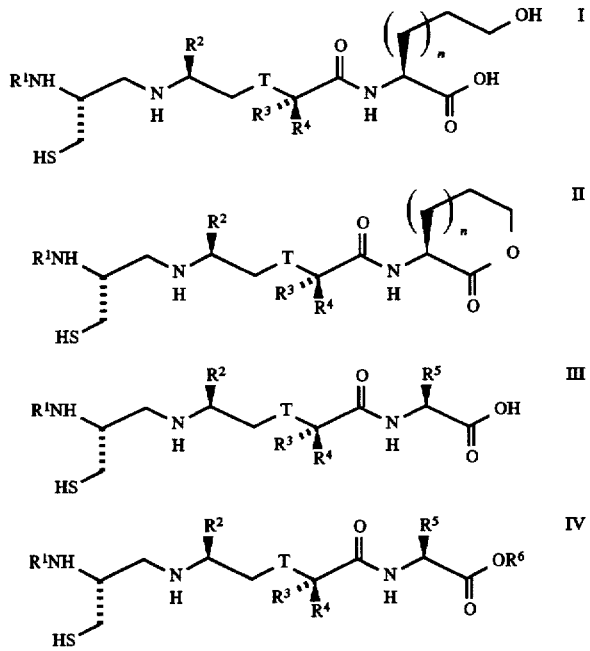

DETAILED DESCRIPTION OF THE INVENTION

The compounds of this invention are useful in the inhibition of farnesyl-protein transferase and the farnesylation of the oncogene protein Ras. In a first embodiment of this invention, the inhibitors of farnesyl-protein transferase are illustrated by the formula I:

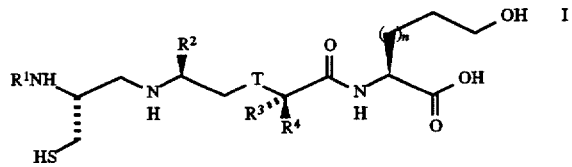

wherein:

R$^1$ is hydrogen, an alkyl group, an aralkyl group, an acyl group, an aracyl group, an aroyl group, an alkylsulfonyl group, aralkylsulfonyl group or arylsulfonyl group, wherein alkyl and acyl groups comprise straight chain or branched chain hydrocarbons of 1 to 6 carbon atoms;

R$^2$ and R$^3$ are the side chains of naturally occurring amino acids, including their oxidized forms which may be methionine sulfoxide or methionine sulfone, or in the alternative may be substituted or unsubstituted aliphatic, aromatic or heteroaromatic groups, such as allyl, cyclohexyl, phenyl, pyridyl, imidazolyl or saturated chains of 2 to 8 carbon atoms which may be branched or unbranched, wherein the aliphatic substituents may be substituted with an aromatic or heteroaromatic ring;

R$^4$ is hydrogen or an alkyl group, wherein the alkyl group comprises straight chain or branched chain hydrocarbons of 1 to 6 carbon atoms;

T is O or S(O)$_m$;

m and n are independently 0, 1 or 2;

or the pharmaceutically acceptable salts thereof.

In a second embodiment of this invention, the prodrugs of compounds of formula I are illustrated by the formula II:

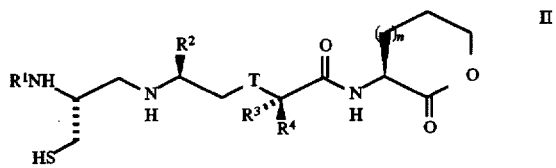

wherein:

R$^1$ is hydrogen, an alkyl group, an aralkyl group, an acyl group, an aracyl group, an aroyl group, an alkylsulfonyl group, aralkylsulfonyl group or arylsulfonyl group, wherein alkyl and acyl groups comprise straight chain or branched chain hydrocarbons of 1 to 6 carbon atoms;

R$^2$ and R$^3$ are the side chains of naturally occurring amino acids, including their oxidized forms which may be methionine sulfoxide or methionine sulfone, or in the alternative may be substituted or unsubstituted aliphatic, aromatic or heteroaromatic groups, such as allyl, cyclohexyl, phenyl, pyridyl, imidazolyl or saturated chains of 2 to 8 carbon atoms which may be branched or unbranched, wherein the aliphatic substituents may be substituted with an aromatic or heteroaromatic ring;

R$^4$ is hydrogen or an alkyl group, wherein the alkyl group comprises straight chain or branched chain hydrocarbons of 1 to 6 carbon atoms;

T is O or S(O)$_m$;

m and n are independently 0, 1 or 2;

or the pharmaceutically acceptable salts and disulfides thereof.

In a third embodiment of this invention, the inhibitors of farnesyl-protein transferase are illustrated by the formula III:

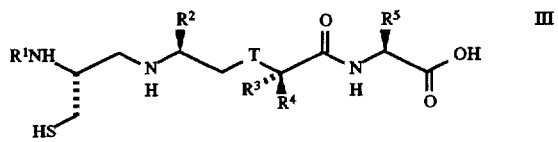

wherein:

R$^1$ is hydrogen, an alkyl group, an aralkyl group, an acyl group, an aracyl group, an aroyl group, an alkylsulfonyl group, aralkylsulfonyl group or arylsulfonyl group, wherein alkyl and acyl groups comprise straight chain or branched chain hydrocarbons of 1 to 6 carbon atoms;

R$^2$, R$^3$ and R$^5$ are the side chains of naturally occurring amino acids, including their oxidized forms which may be methionine sulfoxide or methionine sulfone, or in the alternative may be substituted or unsubstituted aliphatic, aromatic or heteroaromatic groups, such as allyl, cyclohexyl, phenyl, pyridyl, imidazolyl or saturated chains of 2 to 8 carbon atoms which may be branched or unbranched, wherein the aliphatic substituents may be substituted with an aromatic or heteroaromatic ring;

R$^4$ is hydrogen or an alkyl group, wherein the alkyl group comprises straight chain or branched chain hydrocarbons of 1 to 6 carbon atoms;

T is O or S(O)$_m$;

m is 0, 1 or 2;

or the pharmaceutically acceptable salts thereof.

In a fourth embodiment of this invention, the prodrugs of compounds of formula III are illustrated by the formula IV:

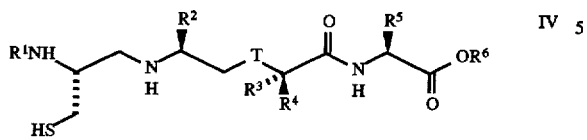

wherein,

- $R^1$ is hydrogen, an alkyl group, an aralkyl group, an acyl group, an aracyl group, an aroyl group, an alkylsulfonyl group, aralkylsulfonyl group or arylsulfonyl group, wherein alkyl and acyl groups comprise straight chain or branched chain hydrocarbons of 1 to 6 carbon atoms;
- $R^2$, $R^3$ and $R^5$ are the side chains of naturally occurring amino acids, including their oxidized forms which may be methionine sulfoxide or methionine sulfone, or in the alternative may be substituted or unsubstituted aliphatic, aromatic or heteroaromatic groups, such as allyl, cyclohexyl, phenyl, pyridyl, imidazolyl or saturated chains of 2 to 8 carbon atoms which may be branched or unbranched, wherein the aliphatic substituents may be substituted with an aromatic or heteroaromatic ring;
- $R^4$ is hydrogen or an alkyl group, wherein the alkyl group comprises straight chain or branched chain hydrocarbons of 1 to 6 carbon atoms;
- $R^6$ is a substituted or unsubstituted aliphatic, aromatic or heteroaromatic group such as saturated chains of 1 to 8 carbon atoms, which may be branched or unbranched, wherein the aliphatic substituent may be substituted with an aromatic or heteroaromatic ring;
- T is O or $S(O)_m$;
- m is 0, 1 or 2;

or the pharmaceutically acceptable salts and disulfides thereof.

The preferred compounds of this invention are as follows:

2(S)-[2(S)-[2(R)-Amino-3-mercapto]propylamino-3(S)-methyl]pentyloxy-3-phenylpropionyl-homoserine lactone, 2(S)-[2(S)-[2(R)-Amino-3-mercapto]propylamino-3(S)-methyl]pentyloxy-3-phenylpropionyl-homoserine, 2(S)-[2(S)-[2(R)-Amino-3-mercapto]propylamino-3(S)-methyl]pentyloxy-2-methyl-3-phenylpropionyl-homoserine lactone, 2(S)-[2(S)-[2(R)-Amino-3-mercapto]propylamino-3(S)-methyl]pentyloxy-2-methyl-3-phenylpropionyl-homoserine, 2(S)-[2(S)-[2(R)-Amino-3-mercapto]propylamino-3(S)-methyl]pentyloxy-4-pentenoyl-homoserine lactone, 2(S)-[2(S)-[2(R)-Amino-3-mercapto]propylamino-3(S)-methyl]pentyloxy-4-pentenoyl-homoserine, 2(S)-[2(S)-[2(R)-Amino-3-mercapto]propylamino-3(S)-methyl]pentyloxypentanoyl-homoserine lactone, 2(S)-[2(S)-[2(R)-Amino-3-mercapto]propylamino-3(S)-methyl]pentyloxypentanoyl-homoserine, 2(S)-[2(S)-[2(R)-Amino-3-mercapto]propylamino-3(S)-methyl]pentyloxy-4-methylpentanoyl-homoserine lactone, 2(S)-[2(S)-[2(R)-Amino-3-mercapto]propylamino-3(S)-methyl]pentyloxy-4-methylpentanoyl-homoserine, 2(S)-[2(S)-[2(R)-Amino-3-mercapto]propylamino-3(S)-methyl]pentyloxy-3-methylbutanoyl-homoserine lactone, 2(S)-[2(S)-[2(R)-Amino-3-mercapto]propylamino-3(S)-methyl]pentyloxy-3-methylbutanoyl-homoserine, 2(S)-[2(S)-[2(R)-Amino-3-mercapto]propylamino-3(S)-methyl]pentyloxy-3-phenylbutanoyl-homoserine lactone, 2(S)-[2(S)-[2(R)-Amino-3-mercapto]propylamino-3(S)-methyl]pentyloxy-3-phenylbutanoyl-homoserine, 2(S)-[2(S)-[2(R)-Amino-3-mercapto]propylamino-3(S)-methyl]pentylthio-2-methyl-3-phenylpropionyl-homoserine lactone, 2(S)-[2(S)-[2(R)-Amino-3-mercapto]propylamino-3(S)-methyl]pentylthio-2-methyl-3-phenylpropionyl-homoserine, 2(S)-[2(S)-[2(R)-Amino-3-mercapto]propylamino-3(S)-methyl]pentylsulfonyl-2-methyl-3-phenylpropionyl-homoserine lactone, 2(S)-[2(S)-[2(R)-Amino-3-mercapto]propylamino-3(S)-methyl]pentylsulfonyl-2-methyl-3-phenylpropionyl-homoserine, 2(S)-[2(S)-[2(R)-Amino-3-mercapto]propylamino-3(S)-methyl]pentyloxy-3-phenylpropionyl-methionine methyl ester, 2(S)-[2(S)-[2(R)-Amino-3-mercapto]propylamino-3(S)-methyl]pentyloxy-3-phenylpropionyl-methionine, 2(S)-[2(S)-[2(R)-Amino-3-mercapto]propylamino-3(S)-methyl]pentyloxy-3-phenylpropionyl-methionine sulfone methyl ester, 2(S)-[2(S)-[2(R)-Amino-3-mercapto]propylamino-3(S)-methyl]pentyloxy-3-phenylpropionyl-methionine sulfone, 2(S)-[2(S)-[2(R)-Amino-3-mercapto]propylamino-3(S)-methyl]pentyloxy-3-phenylpropionyl-methionine sulfone isopropyl ester, 2-(S)-[2(S)-[2(R)-Amino-3-mercapto]propylamino-3(S)-methyl]pentyloxy-3-naphth-2-yl-propionyl-methionine sulfone methyl ester, 2-(S)-[2(S)-[2(R)-Amino-3-mercapto]propylamino-3(S)-methyl]pentyloxy-3-naphth-2-yl-propionyl-methionine sulfone, 2-(S)-[2(S)-[2(R)-Amino-3-mercapto]propylamino-3(S)-methyl]pentyloxy-3-naphth-1-yl-propionyl-methionine sulfone methyl ester, 2-(S)-[2(S)-[2(R)-Amino-3-mercapto]propylamino-3(S)-methyl]pentyloxy-3-naphth-1-yl-propionyl-methionine sulfone, 2-(S)-[2(S)-[2(R)-Amino-3-mercapto]propylamino-3(S)-methyl]pentyloxy-3-methybutanoyl-methionine methyl ester, 2-(S)-[2(S)-[2(R)-Amino-3-mercapto]propylamino-3(S)-methyl]pentyloxy-3-methybutanoyl-methionine, Disulphide of 2(S)-[2(S)-[2(R)-Amino-3-mercapto]propylamino-3(S)-methyl]pentyloxy-3-phenylpropionyl-homoserine lactone, Disulphide of 2(S)-[2(S)-[2(R)-Amino-3-mercapto]propylamino-3(S)-methyl]pentyloxy-3-phenylpropionyl-homoserine, Disulphide of 2(S)-[2(S)-[2(R)-Amino-3-mercapto]propylamino-3(S)-methyl]pentyloxy-3-methylbutanoyl-methionine methyl ester.

or the pharmaceutically acceptable salts thereof.

The most preferred compounds of this invention include the following inhibitor and the corresponding lactone/ester prodrug pairs:

2(S)-[2(S)-[2(R)-Amino-3-mercapto]propylamino-3(S)-methyl]pentyloxy-3-phenylpropionyl-homoserine

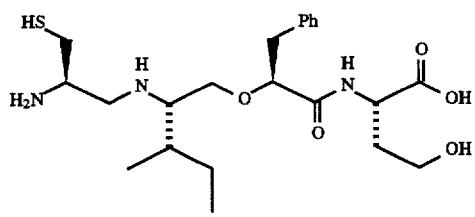

2(S)-[2(S)-[2(R)-Amino-3-mercapto]propylamino-3(S)-methyl]pentyloxy-3-phenylpropionyl-homoserine lactone

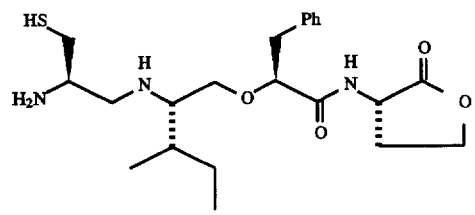

2(S)-[2(S)-[2(R)-Amino-3-mercapto]propylamino-3(S)-methyl]pentyloxy-3-phenylpropionyl-methionine

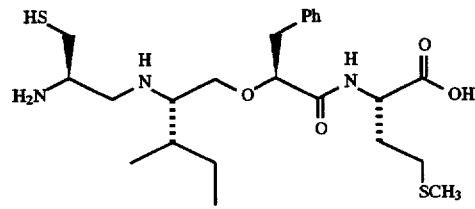

2(S)-[2(S)-[2(R)-Amino-3-mercapto]propylamino-3(S)-methyl]pentyloxy-3-phenylpropionyl-methionine methyl ester

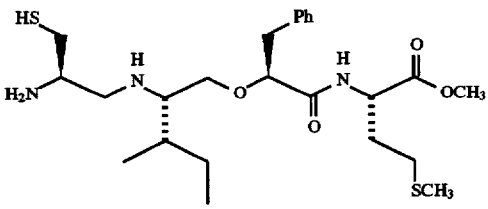

2(S)-[2(S)-[2(R)-Amino-3-mercapto]propylamino-3(S)-methyl]pentyloxy-3-phenylpropionyl-methionine sulfone

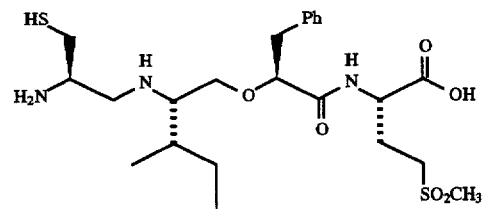

2(S)-[2(S)-[2(R)-Amino-3-mercapto]propylamino-3(S)-methyl]pentyloxy-3-phenylpropionyl-methionine sulfone methyl ester

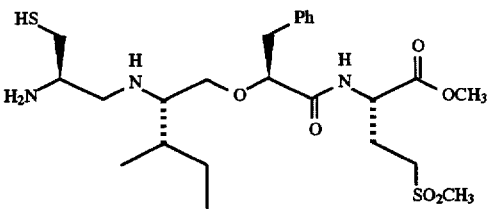

2(S)-[2(S)-[2(R)-Amino-3-mercapto]-propylamino-3(S)-methyl]pentyloxy-3-phenylpropionyl-methionine sulfone isopropyl ester

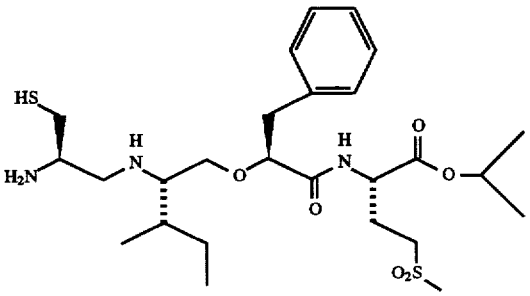

or the pharmaceutically acceptable salts thereof.

As used herein, "alkyl" is intended to include both branched and straight-chain saturated aliphatic hydrocarbon groups having the specified number of carbon atoms.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared by reacting the free base with stoichiometric amounts or with an excess of the desired salt-forming inorganic or organic acid in a suitable solvent or various combinations of solvents.

The compounds of the invention can be synthesized from their constituent amino acids by conventional peptide synthesis techniques, and the additional methods described below. Standard methods of peptide synthesis are disclosed, for example, in the following works: Schroeder et al., "The Peptides", Vol. I, Academic Press 1965, or Bodanszky et al., "Peptide Synthesis", Interscience Publishers, 1966, or McOmie (ed.) "Protective Groups in Organic Chemistry", Plenum Press, 1973, or Barany et al., "The Peptides: Analysis, Synthesis, Biology" 2, Chapter 1, Academic Press, 1980, or Stewart et al., "Solid Phase Peptide Synthesis", Second Edition, Pierce Chemical Company, 1984. The teachings of these works are hereby incorporated by reference.

Abbreviations used in the description of the chemistry and in the Examples that follow are:

| | |
|---|---|
| Ac₂O | Acetic anhydride; |
| Boc | t-Butoxycarbonyl; |
| DBU | 1,8-diazabicyclo[5.4.0]undec-7-ene; |
| DMAP | 4-Dimethylaminopyridine; |
| DME | 1,2-Dimethoxyethane; |
| DMF | Dimethylformamide; |
| EDC | 1(3-dimethylaminopropyl)-3-ethyl-carbodiimide hydrochloride; |
| HOBT | 1-Hydroxybenzotriazole hydrate; |
| Et₃N | Triethylamine; |
| EtOAc | Ethyl acetate. |
| FAB | Fast atom bombardment; |
| HOOBT | 3-Hydroxy-1,2,2-benzotriazin-4(3H)-one; |
| HPLC | High-performance liquid chromatography; |
| MCPBA | m-Chloroperoxybenzoic acid; |
| MsCl | Methanesulfonyl chloride; |
| NaHMDS | Sodium bis(trimethylsilyl)amide |
| Py | Pyridine; |
| TFA | Trifluoroacetic acid; |
| THF | Tetrahydrofuran; |

The oxa isostere compounds of this invention are prepared according to the route outlined in Scheme I. An aminoalcohol 1 is acylated with α-chloroacetyl chloride in the presence of trialkylamines to yield amide 2. Subsequent reaction of 2 with a deprotonation regent (e.g., sodium hydride or potassium t-butoxide) in an ethereal solvent such as THF provides morpholinone 3. The N-Boo derivative 4 is then obtained by the treatment of 3 with BOC anhydride and DMAP (4-dimethylamino-pyridine) in methylene chloride. Alkylation of 4 with R³X, where X is a leaving group such as Br–, I– or Cl– in THF/DME (1,2-dimethoxyethane) in the presence of a suitable base, preferably NaHMDS [sodium bis(trimethylsilyl)amide], affords 5, which is retreated with NaHMDS followed by either protonation or the addition of an alkyl halide R⁴X to give 6a or 6b, respectively. Alternatively, 6a can be prepared from 4 via an aldol condensation approach. Namely, deprotonation of 4 with NaHMDS followed by the addition of a carbonyl compound R⁷R⁸CO gives the adduct 7. Dehydration of 7 can be effected by mesylation and subsequent elimination catalyzed by DBU (1.8-diazabicyclo[5.4.0]undec-7-ene) or the direct treatment of 7 with phosphorus oxy-chloride in pyridine to give olefin 8. Then, catalytic hydrogenation of 8 yields 6a. Direct hydrolysis of 6 with lithium hydrogen peroxide in aqueous THF will produce acid 9b. Sometimes, it is more efficient to carry out this conversion via a 2-step sequence, namely, hydrolysis of 6 in hydrochloric acid to afford 9a, which is then derivatized with BOC-ON or BOC anhydride to give 9b. The peptide coupling of acid 9b with either an α-aminolactone (e.g., homoserine lactone, etc.) or the ester of an amino acid is carried out under the conditions exemplified in the previously described references to yield derivative 10. Treatment of 10 with gaseous hydrogen chloride gives 11, which undergoes reductive alkylation in the presence of aldehyde 12 using sodium cyanoborohydride or similar reducing agents to afford 13. Finally, deprotection of 13 in TFA in the presence of triethylsilane leads to the product 14. Hydrolysis of compounds 14 to the corresponding hydroxy acids and acids, respectively, is accomplished by standard methods such as treatment with NaOH in alcoholic or aqueous milieux followed by careful acidification with dilute HCl.

SCHEME I

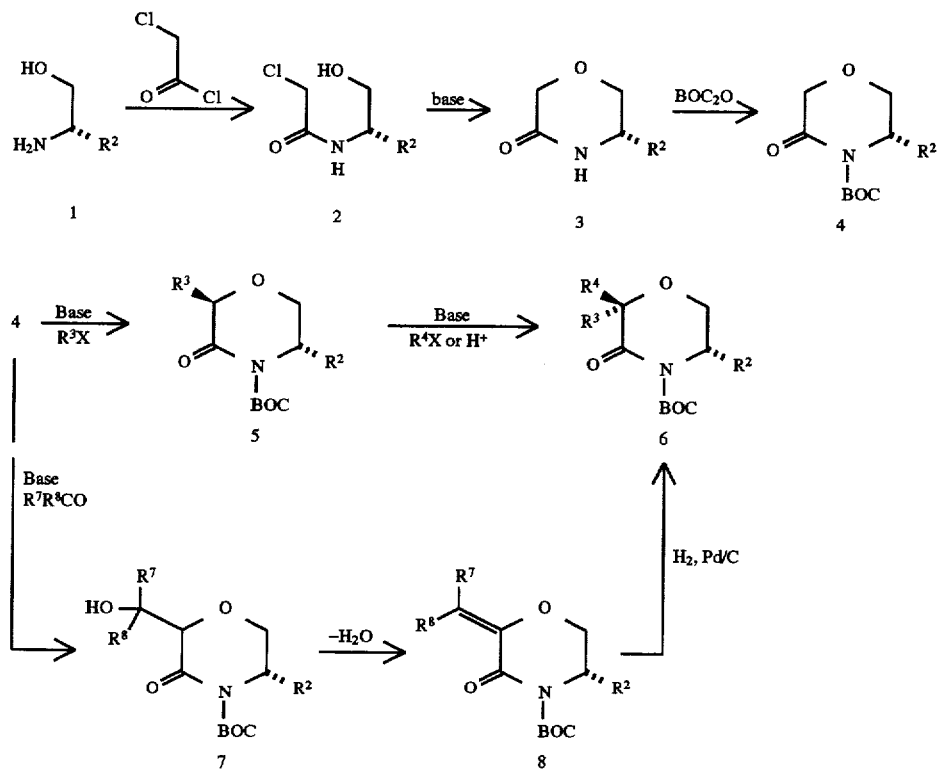

-continued
SCHEME I

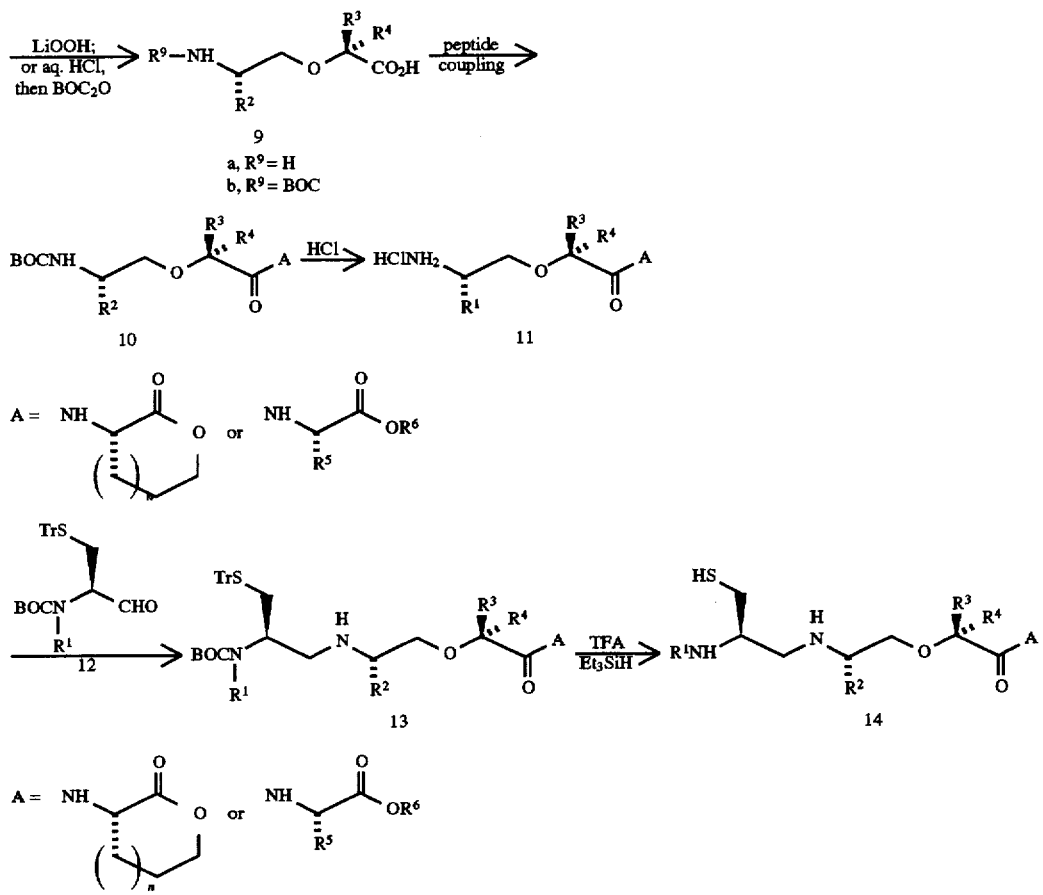

The thia, oxothia and dioxothia isostere compounds of this invention are prepared in accordance to the route depicted in Scheme II. Aminoalcohol 1 is derivatized with $BOC_2O$ to give 15. Mesylation of 15 followed by reaction with methyl a-mercaptoacetate in the presence of cesium carbonate gives sulfide 16. Removal of the BOC group in 16 with TFA followed by neutralization with di-isopropylethylamine leads to lactam 17. N-BOC derivative 18. is obtained via the reaction of 17 with BOC anhydride in THF catalyzed by DMAP. Sequential alkylation of 18 with the alkyl halides $R^3X$ and $R^4X$ in THF/DME using NaHDMS as the deprotonation reagent produces 19. Hydrolysis of 19 in hydrochloride to yield 20a, which is derivatized with Boc anhydride to yield 20b. The coupling of 20b with an a-aminolactone (e.g., homoserine lactone, etc.) or the ester of an amino acid is carried out under conventional conditions as exemplified in the previously described references to afford 21. Sulfide 21 is readily oxidized to sulfone 22 by the use of MCPBA (m-chloroperoxybenzoic acid). The N-BOC group of either 21 or 22 is readily removed by treatment with gaseous hydrogen chloride. The resultant amine hydrochloride 23 undergoes reductive alkylation in the presence of aldehyde 12 using sodium cyanoborohydride or similar reducing agents to yield 24. Finally, deprotection of 24 in TFA in the presence of triethylsilane provides the product 25, which is hydrolyzed to the corresponding hydroxy acid or acid as described for 14.

The compounds of this invention inhibit farnesyl-protein transferase and the farnesylation of the oncogene protein Ras. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

SCHEME II

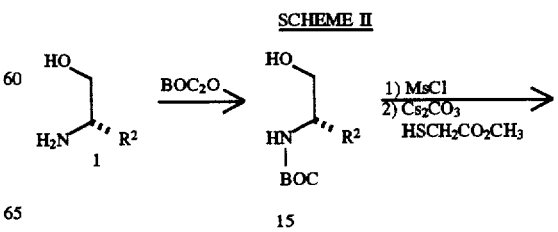

-continued
SCHEME II

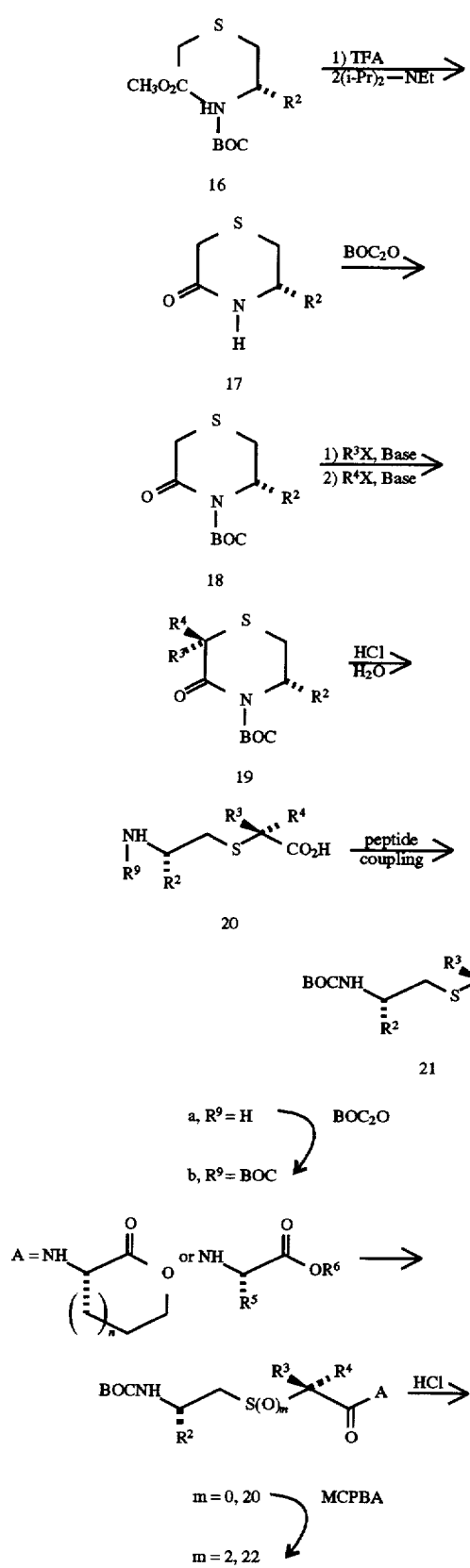

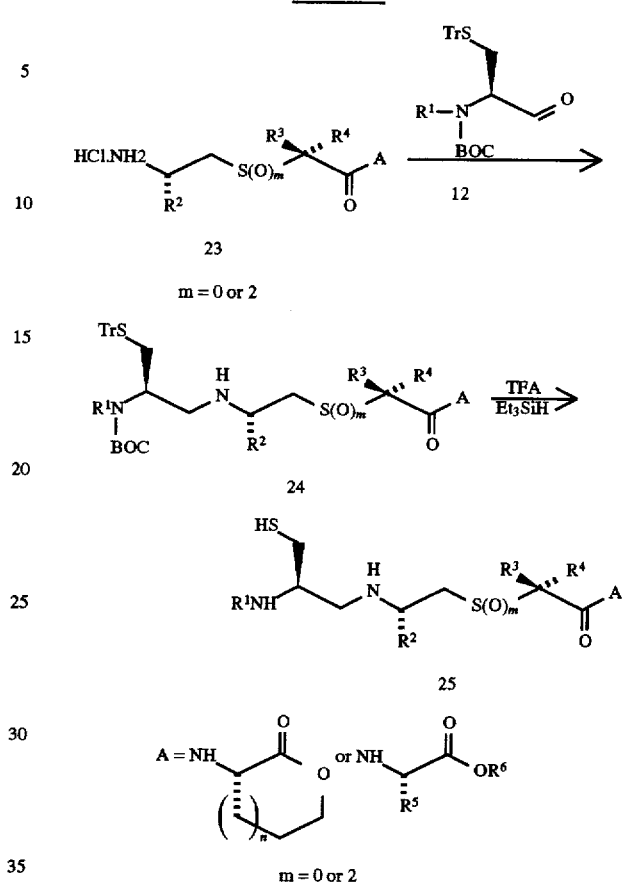

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective mount of the compounds of this invention, with or without pharmaceutically acceptable carriers or diluents. Suitable compositions of this invention include aqueous solutions comprising compounds of this invention and pharmacologically acceptable carriers, e.g. saline, at a pH level, e.g., 7.4. The solutions may be introduced into a patient's intramuscular bloodstream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a human patient undergoing treatment for cancer. Administration occurs in an amount between about 0.1 mg/kg of body weight to about 20 mg/kg of body weight per day, preferably of between 0.5 mg/kg of body weight to about 10 mg/kg of body weight per day.

EXAMPLES

Examples provided are intended to assist in a further understanding of the invention. Particular materials employed, species and conditions are intended to be further illustrative of the invention and not limitative of the reasonable scope thereof.

Example 1

Preparation of 2(S)-[2(S)-[2(R)-Amino-3-mercapto]-propylamino-3(S)-methyl]pentyloxy-3-phenylpropionyl-homoserine lactone and 2(S)-[2(S)-[2(R)-Amino-3-mercapto]-propylamino-3(S)-methyl]pentyloxy-3-phenyl-propionyl-homoserine Step A
Preparation of N-(α-chloroacetyl)-L-isoleucinol To a stirred solution of L-isoleucinol (20 g, 0.17 mol) and triethylamine (28.56 ml, 0.204 mol) in $CH_2Cl_2$ (500 ml) at −78° C. was added chloroacetyl chloride (16.3 ml, 0.204 mol) over 5 minutes. The cooling bath was removed and the solution allowed to warm to −20° C. The mixture was diluted with EtOAc and washed sequentially with 1M HCl, and brine and dried ($Na_2SO_4$). Evaporation in vacuo afforded the amide title compound (35 g, 100%).

Rf=0.3 $CH_2Cl_2$:MeOH (95:5);

$^1$H NMR ($CDCl_3$) δ6.80 (1H, brd, J=5 Hz), 4.10 (2H, s), 3.84 (1H, m), 3.79 (2H, m), 2.65 (1H, brs), 1.72 (1H, m), 1.55 (1H, m), 1.17 (1H, m), 0.96 (3H, d, J=6 Hz) 0.90 (3H, t, J=6 Hz).

Step B
Preparation of 5(S)-[1(S)-methyl]propyl-2,3,5,6-tetrahydro-4H-1,4-oxazin-3-one To a stirred solution of N-(a-chloroacetyl)-L-isoleucinol (7.4 g, 0.038 mol) in THF (125 ml) under argon at 0° C. was slowly added sodium hydride (2.2 g of a 60% dispersion in mineral oil, 0.055 mol) with concomitant gas evolution. After completing the addition, the mixture was warmed to room temperature (R.T.) and stirred for 16 hr. Water (2.8 ml) was added and the solvents evaporated in vacuo. The residue was dissolved in $CHCl_3$ (70 ml) and washed with water saturated NaCl solution. The organic layer was dried ($Na_2SO_4$) and evaporated in vacuo. The residue was chromatographed using silica gel eluting with $CH_2Cl_2$:MeOH (96:4) to afford the lactam title compound (4.35 g, 72%) as a white solid.

Rf=0.35 $CH_2Cl_2$:MeOH (95:5);

$^1$H NMR δ($CDCl_3$) 6.72 (1H, brs), 4.20 (1H, d, J=14.5 Hz), 4.10 (1H, d, J=14.5 Hz), 3.88 (1H, dd, J=9 and 3.5 Hz), 3.58 (1H, dd, J=9 and 6.5 Hz), 3.45 (1H, brqt, J=3.5 Hz), 1.70–1.45 (2H, m), 1.34–1.15 (1H, m), 0.96 (3H, t, J=6.5 Hz), 0.94 (3H, d, J=6.5 Hz).

Step C
Preparation of N-(tert-butoxycarbonyl)-5(S)-[1(S)-methyl]propyl-2,3,5,6-tetrahydro4H-1,4-oxazin-3-one 5(S)-[1(S)-Methyl]propyl-2,3,5,6-tetrahydro 4H-1,4-oxazin-3-one (12.2 g, 0.0776 mol) and DMAP (18.9 g, 0.155 mol) were dissolved in methylene chloride (120 ml) under argon at R.T. Boc anhydride (33.9 g, 0.155 mol) was added to the stirred solution in one portion, with concomitant gas evolution and the mixture was stirred at R.T. for 16 hr. The solvent was evaporated in vacuo and the residue was taken up in ethyl acetate and washed sequentially with 10% citric acid, 50% $NaHCO_3$ and finally brine. The organic extract was dried ($Na_2SO_4$) and evaporated in vacuo. Chromatography of the residue over silica gel eluting with 20% EtOAc in hexanes afforded the title compound (14.1 g, 71%) as a white solid.

Rf=0.75 EtOAc:hexanes (20:80); mp 59°–60° C.

Anal. Calc'd. for $C_{13}H_{23}O_4N$: C, 60.68; H, 9.01; N, 5.44. Found: C, 60.75; H, 9.01; N, 5.58.

$^1$H NMR ($CDCl_3$) δ4.25 (1H, d, J=15 Hz), 4.15–4.00 (2H, m), 3.73 (1H, dd, J=10 and 2 Hz), 1.88 (1H, qt, J=6 Hz), 1.55 (9H, s), 1.50–1.36 (1H, m), 1.35–1.19 (1H, m) 1.00 (3H, d, J=6 Hz) 0.95 (3H, d, J=6.5 Hz).

Step D
Preparation of N-(tert-Butoxycarbonyl)-2(S)-benzyl-5(S)-[1(S)-methyl]propyl-2,3,5,6-tetrahydro-4H-1,4-oxazin-3-one A solution of N-(tert-butoxycarbonyl)-5(S)-[1(S)-methyl]propyl-2,3,5,6-tetrahydro-4H-1,4-oxazin-3-one (5.75 g, 22.34 mmol) in DME (100 ml) under argon was cooled to −60° C. The cold solution was transferred via canula to a second flask containing sodium bis(trimethylsilyl)amide (24.58 ml of a 1M solution in THF, 24.58 mmol) at −78° C. under argon. After stirring for 10 minutes, benzyl bromide (2.25 ml, 18.99 mmol) was added over 5 minutes and the resulting mixture was stirred at −78° C. for 3 hours. After this time, the reaction mixture was transferred via cannula to another flask containing sodium bis(trimethylsilyl)amide (24.58 ml of a 1M solution in THF, 24.58 mmol) at −78° C., under argon. After stirring for a further 5 minutes, the reaction was quenched by the addition of saturated aqueous ammonium chloride solution (24.6 ml) and allowed to warm to room temperature. This mixture was diluted with brine (50 ml) and water (20 ml) and then extracted with ethyl acetate (2×100 ml). The organic extracts were washed with brine (50 ml) and evaporated in vacuo to afford an oil. Chromatography of the residue over silica gel (230–400 mesh, 300 g) eluting with 10–20% ethyl acetate in hexanes afforded the title compound (5.12 g, 67%) as a clear oil.

Rf=0.25 EtOAc:Hexanes (20:80);

$^1$H NMR ($CDCl_3$) δ7.35–7.15 (5H, m), 4.31 (1H, dd, J=6 and 2 Hz), 4.03 (1H, d, J=12 Hz), 3.88 (1H, dd, J=6 and 1 Hz), 3.66 (1H, dd, J=12 and 2 Hz), 3.29 (1H, dd, J=12 and 3 Hz), 1.54 (9H, s), 3.12 (1H, dd, J=12 and 7 Hz), 1.47 (1H, m), 1.25 (1H, m), 1.10 (1H, m), 0.83 (3H, d, J=6 Hz), 0.80 (3H, t, J=6 Hz).

Step E
Preparation of N-(tert-butoxycarbonyl)-2(S)-[2(S)-amino-3(S)-methyl]pentyloxy-3-phenyl-propionic acid To a stirred solution of N-(tert-butoxycarbonyl)-2(S)-benzyl-5(S)-[1(S)-methyl]-propyl-2,3,5,6-tetrahydro-4H-1, 4-oxazin-3-one (5.1 g, 14.7 mmol) in THF (150 ml) and water (50 ml) at 0° C. was added hydrogen peroxide (15 ml of a 30% aqueous solution, 132 mmol) and lithium hydroxide (3.0 g, 63.9 mmol). After stirring for 30 minutes, the reaction was quenched with a solution of sodium sulfite (28.25 g, 0.224 mol) in water (70 ml). The THF was evaporated in vacuo and the aqueous phase was acidified to pH 3–4 by addition of 10% citric acid solution and extracted with EtOAc. The organic extracts were dried ($Na_2SO_4$), evaporated in vacuo and the residue purified by chromatography over silica gel eluting with 4% MeOH in $CH_2Cl_2$ to give the lactam 2(S)-benzyl-5(S)-[1(S)-methyl]propyl-2,3, 5,6-tetrahydro-4H-1,4-oxazin-3-one (0.82 g 22%) and then with 20% MeOH in $CH_2Cl_2$ to afford the title compound (4.03 g, 75%) as a viscous oil.

Rf=0.4 MeOH:$CH_2Cl_2$ (5:95)+0.3% AcOH;

$^1$H NMR (d$_6$ DMSO) δ7.35–7.10 (5H, m), 6.68 (1H, br, s), 3.75 (1H, dd, J=7.5 and 2.5 Hz) 3.54 (1H, m), 3.5–3.2 (2H, m) 2.99 (1H, dd, J=12.5 and 2.5 Hz), 2.75 (1H, dd, J=12.5 and 7.5 Hz), 1.50–1.35 (11H, m), 0.98 (1H, sept, J=6 Hz), 0.78 (3H, t, J=6 Hz), 0.65 (3H, d, J=6 Hz);

FAB MS 366 (MH+) 266 ($MH_2^+$-$CO_2^tBu$).

Step F

Preparation of N-(tert-butoxycarbonyl)-2(S)-[2(S)-amino-3 (S)-methyl]-pentyloxy-3-phenyl-propionyl-homoserine lactone To a stirred solution of N-(tert-butoxycarbonyl)-2(S)-[2 (S)-amino-3(S)-methyl]-pentyloxy-3-phenylpropionic acid (0.53 g, 1.45 mmol) and 3-hydroxy-1,2,3,-benzotriazin-4 (3H)-one (HOOBT) (0.26 g, 1.6 mmol) in DMF (15 ml) at room temperature was added EDC (0.307 g, 1.6 mmol) and L-homoserine lactone hydrochloride (0.219 g, 6.0 mmol). The pH was adjusted to pH=6.5 by addition of NEt$_3$ (the pH was monitored by application of an aliquot of the reaction mixture to a moist strip of pH paper). After stirring at room temperature for 16 hr, the reaction was diluted with EtOAc and washed with saturated NaHCO$_3$ and then brine and dried (NaSO$_4$). Evaporation in vacuo (sufficient to remove DMF) and chromatography over silica gel eluting with 5 % acetone in CH$_2$Cl$_2$ afforded the title compound (520 mg, 80%) as a white solid, mp 115°14 117° C.

Rf=0.3 Acetone: CH$_2$Cl$_2$ (5:95).

$^1$H NMR (CDCl$_3$) δ7.73 (1H, brd, J=5 Hz), 7.40–7.15 (5H, m), 4.68 (1H, dt, J=9 and 7.5 Hz), 4.65–4.35 (2H, m), 4.33–4.18 (1H, m), 4.20 (1H, dd, J=7 and 3 Hz), 3.78 (1H, m), 3.49 (1H, dd, J=7.5 and 4.0 Hz), 3.37 (1H, dd, J=7.5 and 6.5 Hz), 3.15 (1H, dd, J=11.5 and 2 Hz), 2.86 (1H, dd, J=11.5 and 7.5 Hz), 2.68 (1H, m) 2.11 (1H, q, J=9 Hz), 1.55–1.30 1.30 (11H, m), 1.07 (1H, m), 0.87 (3H, t, J=6.3 Hz), 0.79 (3H, d, J=6 Hz).

Step G

Preparation of 2(S)-[2(S)-amino-3(S)-methyl]-pentyloxy-3-phenylpropionyl-homoserine lactone hydrochloride Anhydrous HCl gas was bubbled through a cold (0° C.) solution of N-(tert-butoxycarbonyl)-2(S)-[2(S)-amino-3(S)-methyl]pentyloxy-3-phenylpropionyl-homoserine lactone (3.0 g, 6.7 mmol) in ethyl acetate (120 ml) until a saturated solution was obtained. The resulting mixture was stirred at 0° C. for 1 hr. The solution was purged with nitrogen and the mixture concentrated in vacuo to afford the title compound as a sticky foam which was used without further purification.

$^1$H NMR (d$_6$ DMSO) δ8.60 (1H, d, J=7 Hz), 8.08 (3H, brs), 7.35–7.15 (5H, m), 4.60 (1H, qt, J=8 Hz), 4.36 (1H, t J=7.5 Hz), 4.22 (1H, q, J=7.5 Hz), 4.15–3.95 (2H, m), 3.64 (1H, dd, J=9 and 2.5 Hz), 3.15–3.00 (2H, m), 2.92 (1H, dd, J=12.5 and 5.0 Hz), 2.40–2.15 (2H, m), 1.65 (1H, m), 1.43 (1H, m), 1.07 (1H, m), 0.82 (3H, t, J=6 Hz), 0.72 (3H, d, J=6.0 Hz).

Step H

Preparation of 2(S)-[2(S)-[2(R)-(tert-butoxycarbonyl)-amino-3-triphenylmethylmercap-to]propylamino-3(S)-methyl]pentyloxy-3-phenylpropionyl-homoserine lactone 2(S)-[2(S)-Amino-3(S)-methyl]pentyloxy-3-phenylpropionyl-homoserine hydrochloride (6.7 mmol) and N-(tert-butoxycarbonyl)-S-triphenylmethylcysteine aldehyde (0.74 g, 7.5 mmol) (prepared from N-(tert-butoxycarbonyl)-S-triphenylmethylcysteine by the procedure of Goel, O. P.; Krolls, U.; Stier, M.; Keston, S. *Org. Syn.* 1988, 67, 69.) and potassium acetate (3.66 g, 8.2 mmol) were dissolved in methanol (48 ml). Activated 4A molecular sieves (6 g) and then Na(CN)BH$_3$ (0.70 g, 10.7 mmol) were added and the resulting slurry was stirred under argon at room temperature for 16 hr. The solids were removed by filtration and the filtrate evaporated in vacuo. The residue was dissolved in EtOAc and washed sequentially with saturated aqueous NaHCO$_3$ and brine and then dried (Na$_2$SO$_4$). Evaporation in vacuo afforded an oil which was purified by chromatography over silica gel eluting with a gradient of 30–50% EtOAc in hexane to afford the title compound (2.34 g, 45%) contaminated with a small amount of the corresponding methyl ester.

$^1$H NMR (CD$_3$OD) δ7.60–7.05(20H, m), 4.64 (1H, d, J=9.0 Hz), 4.39 (1H, br t, J=9 Hz), 4.25(1H, m), 3.93 (1H, m), 3.75–3.60(1H, m), 3.55 (1H, dd, J=9.0 and 2 Hz), 3.20 (1H, dd, J=9.0 and 6.0 Hz), 3.04 (1H, dd, J=15.0 and 5.0 Hz), 2.85 (1H, dd, J=15.0 and 9.0 Hz), 2.60 (1H, dd, J=12.0 and 5.0 Hz), 2.50–2.15 (7H, m), 1.45 (9H, s), 1.40–1.20 (1H, m), 1.07 (1H, m), 0.87 (3H, t, J=6 Hz), 0.67 (3H, d, J=6.0 Hz).

Step I

Preparation of 2(S)-[2(S)-[2(R)-Amino-3-mercapto] propylamino-3(S)-methyl]pentyloxy-3-phenylpropionyl-homoserine lactone To a stirred solution of 2(S)-[2(S)-[2(R)-(tert-butoxycarbonyl) amino-3-triphenylmethylmercapto]-propylamino-3(S)-methyl]pentyloxy-3-phenylpropionyl-homoserine lactone (2.72 g, 3.49 mmol) in CH$_2$Cl$_2$ (90 ml) was added HSiEt$_3$ (2.16 ml, 13.5 mmol) and TFA (43.2 ml, 0.56 mol) and the solution was stirred at R.T. under argon for 2 hrs. The solvent was evaporated in vacuo and the residue partitioned between 0.1% aqueous TFA (200 ml) and hexanes (100 ml). The aqueous layer was separated and washed with hexanes (20 ml) and then lyophilised. The resulting white lyophilate was chromatographed in 5 equal portions over a Waters Prepak cartridge (C-18, 15–20 mM 100 A) eluting with a gradient of 95:5 to 5:95 0.1% TFA in H$_2$O:0.1% TFA in CH$_3$CN at 100 ml/min over 60 min. The desired compound eluted after 19 min. The CH$_3$CN was evaporated in vacuo and the aqueous solution lyophilised to afford the title compound (1.95 g, 77%) as the TFA salt.

The salt is hygroscopic and is prone to disulphide formation if left in solution and exposed to air.

$^1$H NMR δ(CD$_3$OD) 7.40–7.15 (5H, m), 4.55–5.40 (2H, m), 4.33 (1H, m), 4.18 (1H, m), 3.90–3.62 (3H, m), 3.53 (1H, dd, J=10.5 and 4.0 Hz), 3.37 (1H, dd, J=10.5 and 6.0 Hz), 3.23 (1H, m), 3.15–2.95 (2H, m), 2.88 (1H, dd, J=12.5 and 5.0 Hz), 2.55–2.25 (2H, m), 1.92 (1H, m), 1.49 (1H, m), 1.23 (1H, m), 0.94 (3H, t, J=6 Hz), 0.90 (3H, d, J=6 Hz). FAB MS 873 (2M–H$^+$) 438 (MH$^+$) 361 (MH±Ph)

Anal. calc'd for C$_{22}$H$_{36}$O$_4$N$_3$S 2.6 TFA:C, 43.58; H, 5.25; N, 5,82. Found: C, 43.62; H, 5.07; N, 5.80.

Step J

Preparation of 2(S)-[2(S)-[2(R)-Amino-3-mercapto] propylamino-3(S)-methyl]pentyloxy-3-phenylpropionyl-homoserine 2(S)-[2(S)-[2(R)-Amino-3-mercapto]propyl-amino-3(S)-methyl]pentyloxy-3-phenylpropionyl-homoserine lactone (0.00326 mmol) was dissolved in methanol (0.0506 ml) and 1N sodium hydroxide (0.0134 ml) was added followed by methanol (0.262 ml). The conversion of the lactone to the hydroxy-acid was confirmed by HPLC analysis and NMR.

Example 2

Preparation of 2(S)-[2(S)-[2(R)-Amino-3-mercapto]-propylamino-3(S)-methyl]pentyloxy-2-methyl-3-phenyl-propionyl-homoserine lactone and 2(S)-[2(S)-[2(R)-Amino-3-mercapto]propylamino-3(S)-methyl]pentyloxy-2-methyl-3-phenyl-propionyl-homoserine

Step A
Preparation of N-(tert-butoxycarbonyl)-2(S)-benzyl-2-methyl-5(S)-[1(S)-methyl]-propyl-2,3,5,6-tetrahydro-4H-1,4-oxazin3-one A solution of N-(tert-butoxycarbonyl)-5(S)-[1(S)-methyl] propyl-2,3,5,6-tetrahydro-4H-1,4-oxazin-3-one (1.0 g, 3.89 mmol) in DME (12.6 ml) was cooled to −60° C. under argon, then transferred via a cannula to a flask containing 4.27 ml of 1.0M NaHMDS solution in THF. The resulting mixture was stirred under argon at −78° C. for 5 min. followed by the treatment of benzyl bromide (0.42 ml, 3.5 mmol). The mixture was stirred at −78° C. for 0.5 hr, then warmed to −50° C. and stirred for 0.5 h. It was recooled to −78° C. and methyl iodide (0.48 ml, 7.78 mmol) was added. After 10 min of stirring, the mixture was added via cannula to a stirred solution of NaHMDS (1.0M in THF, 4.27 ml) at −78° C. The final mixture was stirred at −78° C. for 10 min. before the addition of brine and ether. The organic layer was separated, dried, filtered and evaporated to yield a residue which was purified by flash chromatography to afford the title compound.

NMR (CDCl$_3$) δ0.63 (3H, t, J=7 Hz), 0.69 (3H, d, J=7 Hz), 0.85 (H, m), 1.01 (2H, m), 1.49 (3H, s), 1.53 (9H, s), 2.86 (H, d, J=12 Hz), 3.32 (H, d, J=12 Hz), 3.74 (H, m), 3.82 (2H, s), 7.25 (5H, m).

Step B
Preparation of N-(tert-butoxycarbonyl)-2(S)-[2(S)-amino-3 (S)-methyl]pentyloxy-2-methyl-3-phenylpropionic acid A mixture of N-(tert-butoxycarbonyl)-2(S)-benzyl-2-methyl-5(S)-[1(S)-methyl]propyl-2,3,5,6-tetrahydro-4H-1,4-oxazin-3-one (0.41 g, 1.13 mmol), concentrated hydrochloric acid (4 ml) and acetic acid (4 ml) was heated at reflux overnight. After cooling, the mixture was evaporated to dryness and the residue was mixed with Boc-ON (0.417 g) and dissolved in acetone (5 ml) and water (5 ml). The pH value of the mixture was then adjusted to 9 by the addition of triethylamine and stirred at room temperature overnight. The reaction mixture was evaporated to dryness and the residue was treated with 10% citric acid solution (20 ml) and extracted with methylene chloride twice (2×25 ml). The combined extracts were washed with water, dried, filtered and evaporated to leave a residue which was purified by flash chromatography to afford the title compound (0.295 g, 0.78 mmol, 69%).

NMR (DMSO-d$_6$) δ0.78 (3H, d, J=7 Hz), 0.83 (3H, t, J=7 Hz), 1.18 (3H, s), 1.40 (9H, s), 1.57 (H, m), 3.85 (H, d, J=12 Hz), 3.98 (H, d, J=12 Hz), 6.65 (H, m), 7.23 (5H, m).

Step C
Preparation of N-(tert-Butoxycarbonyl)-2(S)-2(S)-amino-3 (S)-methyl]pentyloxy-2-methyl-3-phenylpropionyl-homoserine lactone The title compound was prepared in a similar fashion as that described in Example 1, Step F, but using N-(tert-butoxycarbonyl)-2(S)-[2(S)-amino-3(S)-methyl]pentyloxy-2-methyl 3-phenylpropionic acid instead of N-(tert-butoxycarbonyl)-2(S)-[2(S)-amino-3(S)-methyl]pentyloxy-3-phenylpropionic acid. NMR (CDCl$_3$) δ0.89 (3H, d, J=7 Hz), 0.90 (3H, t, J=7 Hz), 1.13 (H, m), 1.43 (12H, s), 1.92 (H, m), 2.51 (H, m), 2.90 (H, d, J=12 Hz), 3.03 (H, d, J=12 Hz), 3.40 (H, m), 3.57 (H, d of d, J=10, 6 Hz), 3.73 (H, m), 4.24 (H, m), 4.35–4.48 (2H, m), 4.58 (H, m), 7.23 (5H, m), 7.63 (H, m).

Step D
Preparation of 2(S)-[2(S)-amino-3(S)-methyl]-pentyloxy-2-methyl-3-phenylpropionyl-homoserine lactone hydrochloride The title compound was prepared in a similar fashion as that described in Example 1, Step G, but using N-(tert-butoxycarbonyl)-2(S)-[2(S)-amino-3(S)-methyl]pentyloxy-2-methyl-3-phenylpropionyl-homoserine lactone in place of N-(tert-butoxycarbonyl)-2(S)-[2(S)-amino-3(S)-methyl] pentyloxy-3-phenylpropionyl-homoserine lactone. NMR (DMSO-d$_6$) δ0.79 (3H, d, J=7 Hz), 0.85 (3H, t, J=7 Hz), 1.15 (H, m), 1.33 (3H, s), 1.48 (H, m), 1.70 (H, m), 2.15 (H, m), 2.32 (H, m), 2.97 (H, d, J=12 Hz), 3.07 (H, d, J=12 Hz), 3.16 (H, m), 3.52 (H, m), 3.65 (H, d of d, J=10, 3 Hz), 4.26 (H, m), 4.37 (H, m), 4.65 (H, q, J=8 Hz,), 7.24 (5H, m), 8.44 (H, d, J=8 Hz).

Step E
Preparation of 2(S)-[2(S)-[2(R)-(tert-Butoxy-carbonyl) amino-3-triphenylmethylmercapto]propylamino-3(S)-methyl]pentyloxy-2-methyl-3-phenylpropionyl-homoserine lactone The title compound was prepared in the same manner as that described in Example 1, Step H, but using 2(S)-[2(S)-amino-3(S)-methyl]pentyloxy-2-methyl-3-phenylpropionyl-homoserine lactone hydrochloride in place of 2(S)-[2(S)-amino-3(S)-methyl]pentyloxy-3-phenylpropionyl-homoserine lactone hydrochloride.

Step F
Preparation of 2(S)-[2(S)-[2(R)-Amino-3-mercapto] propylamino-3(S)-methyl]pentyloxy-2-methyl-3-phenylpropionyl-homoserine lactone The title compound was prepared in a similar fashion as that described in Example 1, Step I, but using 2(S)-[2(S)-[2(R)-(tert-butoxycarbonyl)butoxycarbonyl) amino-3-triphenylmethylmercapto]propylamino-3(S)-methyl] pentyloxy-2-methyl-3-phenylpropionyl-homoserine lactone in place of 2(S)-[2(S)-[2(R)-(tert-butoxycarbonyl)amino-3-triphenylmethylmercapto]propylamino-3(S)-methyl] pentyloxy-3-phenylpropionyl-homoserine lactone. NMR (CD$_3$OD) δ0.99 (3H, t, J=7 Hz), 1.02 (3H, d, J=7 Hz), 1.30 (H, m), 1.49 (H, m), 1.52 (3H, s), 1.62 (H, m), 1.94 (H, m), 2.30–2.50 (2H, m), 2.86 (H, d of d, J=15, 7 Hz), 3.04 (2H, s), 3.20 (H, m), 3.42 (H, d of d, J=14,6 Hz), 3.62 (H, d of d, J=11.3 Hz), 3.68–3.85 (2H, m), 4.34 (H, m), 4.48 (2H, m), 7.25 (5H, m).

Anal. Calcd for C$_{23}$H$_{37}$N$_3$O$_4$S.2.15CF$_3$CO$_2$H.0.5H$_2$O:C, 46.46; H, 5.73; N, 5.94 Found: C, 46.49; H, 5.75; N, 5.85.

Step G
Preparation of 2(S)-[2(S)-[2(R)-Amino-3-mercapto] propylamino-3(S)-methyl]pentyloxy-2-methyl-3-phenylpropionyl-homoserine The title compound was prepared in a similar fashion as that described in Example 1, Step J, but using 2(S)-[2(S)-[2(R)-amino-3-mercapto]propylamino-3(S)-methyl] pentyloxy-2-methyl-3-phenylpropionyl-homoserine lactone in place of 2(S)-[2(S)-[2(R)-amino-3-mercapto] propylamino-3(S)-methyl]pentyloxy-3-phenylpropionyl-homoserine lactone.

Example 3

Preparation of 2(S)-[2(S)-[2(R)-Amino-3-mercapto]-propylamino-3(S)-methyl]pentyloxy 4-pentenoyl-homoserine lactone and 2(S)-[2(S)-[2(R)-Amino-3-mercapto]propylamino-3(S)-methyl]pentyloxy-4-pentanoyl-homoserine

Step A
Preparation of N-(tert-Butoxycarbonyl)-2(S)-allyl-5(S)-[1 (S)-methyl]propyl-2,3,5,6-tetra-hydro-4H-1,4-oxazin-3-one The title compound was prepared in a similar fashion as that described in Example 1, Step D, but using allyl bromide instead of benzyl bromide. NMR (CDCl$_3$) δ0.94 (3H, t, J=7 Hz), 1.00 (3H, d, J=7 Hz), 1.24 (H, m), 1.43 (H, m), 1.54 (9H, s), 1.85 (H, m), 2.55 (H, m), 2.76 (6H, m), 3.72 (H, d of d, J=13.3 Hz), 3.96 (H, m), 4.07–4.17 (2H, m), 5.10 (H, d, J=12 Hz), 5.18 (H, d of d, J=12.2 Hz), 5.86 (H, m).

Step B

Preparation of N-(tert-Butoxycarbonyl)-2(S)-[2(S)-amino-3 (S)-methyl]pentyloxy-4-pentenoic acid The title compound was prepared in a similar fashion as that described in Example 1, Step E, but using N-(tert-butoxycarbonyl)-2(S)-allyl-5(S)-[1(S)-methyl[propyl-2,3, 5,6 -tetrahydro-4H-1,4-oxazin-3-one in place of N-(tert-butoxycarbonyl)-2(S)-benzyl-5(S)-[1(S)-methyl]propyl-2,3, 5,6-tetrahydro-4H-1,4-oxazin-3-one. NMR (DMSO-$d_6$) $\delta 0.80$ (3H, d, J=7 Hz), 0.82 (3H, t, J=7 Hz), 1.05 (H, m), 1.38 (9H, s), 1.52 (H, m), 2.25 (H, m), 2.39 (H, m), 3.55 (2H, m), 4.96 (H, d, J=10 Hz), 5.02 (H, d, J=17 Hz), 5.85 (H, m), 6.73 (H, m).

Step C

Preparation of N-(tert-Butoxycarbonyl)-2(S)-[2(S)-amino-3 (S)-methyl]pentyloxy-4-pentenoyl-homoserine lactone The title compound was prepared in a similar fashion as that described in Example 1, Step F, but using N-(tert-butoxycarbonyl)-2(S)-[2(S)-amino-3(S)-methyl]pentyloxy-4-pentenoic acid in place of N-(tert-butoxycarbonyl-2(S)-[2 (S)-amino-3(S)-methyl]pentyl-oxy-3-phenylpropionic acid. NMR (CDCl$_3$) $\delta 0.90$ (3H, t, J=7 Hz), 0.91 (3H, d, J=7 Hz), 1.14 (H, m), 1.44 (9H, s), 2.32 (H, m), 2.44 (H, m), 2.5–2.7 (2H, m), 3.56 (2H, m), 3.75 (H, m), 3.90 (H,4.28 (H, m), 4.44–4.55 (2H, m), 4.70 (H, m), 5.05–5.13 (2H, m), 5.80 (H, m), 7.94 (H, m).

Step D

Preparation of 2(S)-[2(S)-Amino-3(S)-methyl]-pentyloxy-4-pentenoyl-homoserine lactone hydrochloride The title compound was prepared in a similar fashion as that described in Example 1, Step G, but using N-(tert-butoxycarbonyl)-2(S)-[2(S)-amino-3(S)-methyl]pentyloxy-4-pentenoyl-homoserine lactone in place of N-(tert-butoxycarbonyl)-2(S)-[2(S)-amino-3(S)-methyl]pentyloxy-3-phenylpropionyl-homoserine lactone. NMR (CDCl$_3$) $\delta 0.96$ (3H, t, J=7 Hz), 1.02 (3H, d, J=7 Hz), 1.23 (H, m), 1.62 (H, m), 1.77 (2H, m), 2.05 (H, m), 2.50 (H, m), 2.64 (2H, m), 3.30 (H, m), 3.82 (H, m), 3.91 (H, m), 4.07 (H, m), 4.30 (H, m), 4.52 (H, m), 4.90 (H, m), 5.09 (H, d, J=10 Hz), 5.16 (H, d, J=18 Hz), 5.85 (H, m), 8.70 (H, m).

Step E

Preparation of 2(S)-[2(S)-[2(R)-(tert-Butoxy-carbonyl) amino-3-triphenylmethylmercapto]pro-pylamino-3(S)-methyl]pentyloxy-4-pentenoyl-homoserine lactone The title compound was prepared in a similar fashion as that described in Example 1, Step H, but using 2(S)-[2(S)-amino-3(S)-methyl]pentyloxy-4-pentenoyl-homoserine lactone hydrochloride in place of 2(S)-[2(S)-amino-3(S)-methyl]pentyloxy-3-phenyl-propionyl-homoserine lactone hydrochloride. NMR (CDCl$_3$) $\delta 0.83$ (3H, t, J=7 Hz), 0.91 (3H, t, J=7 Hz), 1.47 (9H, s), 3.80 (H, m), 4.23 (H, m), 4.27 (H, m), 5.10–5.15 (2H, m), 5.80 (H, m), 7.15–7.50 (15H, m).

Step F

Preparation of 2(S)-[2(S)-[2(R)-Amino-3-mercapto] propylamino-3(S)-methyl]-pentyloxy-4-pentenoyl-homoserine lactone The title compound was prepared in a similar fashion as that described in Example 1, Step I, but using 2(S)-[2(S)-[2(R)-(tert-butoxycarbonyl)amino-3-triphenylmethylmercapto]propylamino-3(S)-methyl] pentyloxy-4-pentenoyl-homoserine lactone in place of 2(S) -[2(S)-[2(R)-(tert-butoxycarbonyl)-amino-3-triphenylmethyl-mercapto]propylamino-3(S)-methyl] pentyloxy-3-phenylpropionyl-homoserine lactone. NMR (CD$_3$OD) $\delta 0.99$ (3H, t, J=7 Hz), 1.04 (3H, d, J=7 Hz), 1.34 (H, m), 1.55 (H, m), 1.75 (H, m), 1.93 (2H, m), 2.40 (H, m), 2.52 (2H, m), 2.68 (H, m), 2.8–3.1 (2H, m), 3.56 (H, m), 4.03 (H, m), 4.34 (H, m), 4.50 (2H, m), 5.08–5.20 (2H, m), 5.85 (H, m).

Step G

Preparation of 2(S)-[2(S)-[2(R)-Amino-3-mercapto] propylamino-3(S)-methyl]pentyloxy-4-pentanoyl-homoserine The title compound was prepared in a similar fashion as that described in Example 1, Step J, but using 2(S)-[2(S)-[2(R)-amino-3-mercapto]propylamino-3(S)-methyl] pentyloxy-4-pentanoyl-homoserine lactone in place of 2(S) -[2(S)-[2(R)-amino-3-mercapto]propylamino-3(S)-methyl] pentyloxy-3-phenylpropionyl-homoserine lactone.

Example 4

Preparation of 2(S)-[2(S)-[2(R)-Amino-3-mercapto]-propylamino-3(S)-methyl]pentyloxypentanoyl-homoserine lactone and 2(S)-[2(S)-[2(R)-Amino-3-mercapto] propylamino-3(S)-methyl]-pentyloxypentanoyl-homoserine Step A Preparation of N-(tert-Butoxycarbonyl)-2(S)-[2(S)-Amino-3(S)-methyl]-pentyloxypentanoyl-homoserine lactone A mixture of N-(tert-Butoxycarbonyl)-2(S)-[2-(S)-amino-3(S)-methyl]pentyloxy-4-pentenoyl-homoserine lactone (87 mg, 0.22 mmol) and 10% Pd/C (10 mg) in ethyl acetate (10 ml) was hydrogenated at 1 atm for 2 h. The catalyst was then removed by filtration and the filtrate was concentrated to give the title compound (82 mg, 0.20 mmol, 91%) as a gum. NMR (CDCl$_3$) $\delta 0.85$–0.97 (9H, m), 1.15 (H, m), 1.42 (9H, s), 2.33 (H, m), 2.64 (H, m), 3.55 (2H, m), 3.76 (H, m), 3.84 (H, m), 4.29 (H, m), 4.45–4.60 (2H, m), 4.70 (H, m), 7.93 (H, m).

Step B

Preparation of 2(S)-[2(S)-Amino-3(S)-methyl]-pentyloxypentanoyl-homoserine lactone hydrochloride The title compound was prepared in a similar fashion as that described in Example 1, Step G, but using N-(tert-butoxycarbonyl)-2(S)-2(S)-amino-3(S)-methyl] pentyloxypentanoyl-homoserine lactone in place of N-(tert-butoxycarbonyl)-2(S)-[2(S)-amino-3(S)-methyl]pentyloxy-3-phenylpropionyl-homoserine lactone. NMR (CDCl$_3$) $\delta 0.89$–1.00 (6H, m), 1.02 (3H, d, J=7 Hz), 1.87 (H, m), 2.05 (H, m), 2.52 (H, m), 2.68 (H, m), 3.30 (H, m), 3.77 (H, d of d, J=8.2 Hz), 3.86 (H, m), 3.98 (H, t, J=5 Hz), 4.30 (H, m), 4.53 (H, t, J=10 Hz), 4.91 (H, m), 8.73 (H, d, J=9 Hz).

Step C

Preparation of 2(S)-[2(S)-[2(R)-(tert-Butoxy-carbonyl) amino-3-triphenylmethylmercapto]pro-pylamino-3(S)-methyl]pentyloxy-pentanoyl-homoserine lactone The title compound was prepared in a similar fashion as that described in Example 1, Step H, but using 2(S)-[2(S)-amino-3(S)-methyl]pentyloxypentanoyl-homoserine lactone hydrochloride in place of 2(S)-[2(S)-amino-3(S)-methyl]pentyloxy-3-phenyl-propionyl-homoserine lactone hydrochloride.

Step D

Preparation of 2(S)-[2(S)-[2(R)-Amino-3-mercapto] propylamino-3(S)-methyl]pentyloxy-pentanoyl-homoserine lactone The title compound was prepared in the same manner as that described in Example 1, Step I, but using 2(S)-[2(S)-[2(R)-(tert-butoxycarbonyl)-amino-3-triphenylmethylmercapto]propylamino-3(S)-methyl] pentyloxy-pentanoyl-homoserine lactone in place of 2(S)-[2(S)-[2(R)-(tert-butoxycarbonyl)amino-3- triphenylmethylmercapto]propylamino- 3(S)-methyl]-pentyloxy-3-phenylpropionyl-homoserine lactone. NMR (CD$_3$OD) δ0.97~1.13 (9H, m), 1.36 (H, m), 1.51 (2H, m), 1.61 (H, m), 1.75 (H, m), 1.99 (H, m), 2.45 (H, m), 2.59 (H, m), 2.9~3.1 (2H, m), 4.00 (H, m), 4.37 (H, m), 4.55 (H, m). Anal. Calcd for C$_{18}$H$_{35}$N$_3$O$_4$S.2.6CF$_3$CO$_2$H.0.45H$_2$O:C, 40.15;H, 5.59; N, 6.05. Found: C, 40.16; H, 5.60; N, 6.05.

Step E

Preparation of 2(S)-[2(S)-[2(R)-Amino-3-mercapto]propylamino-3(S)-methyl]-pentyloxy-pentanoyl-homoserine The title compound was prepared in the same manner as that described in Example 1, Step J, but using 2(S)-[2(S)-[2(R)-amino-3-mercapto]propylamino-3(S)-methyl]pentyloxypentanoyl-homoserine lactone in place of 2(S)-[2(S)-[2(R)-amino-3-mercapto]propylamino-3(S)-methyl]pentyloxy-3-phenylpropionyl-homoserine lactone.

Example 5

Preparation of 2(S)-[2(S)-[2(R)-Amino-3-mercapto]-propylamino-3(S)-methyl]pentyloxy-4-methylpentanoyl-homoserine lactone and 2(S)-[2(S)-[2(R)-amino-3-mercapto]propylamino-3(S)-methyl]pentyloxy-4-methyl-pentanoyl-homoserine Step A Preparation of N-(tert-Butoxycarbonyl)-2(S)-methylallyl-5(S)-[1(S)-methyl]propyl-2,3,5,6-tetrahydro-4H-1,4-oxazin-3-one The title compound was prepared in a similar fashion as that described in Example 1, Step D, but using methallyl bromide in place of benzyl bromide. NMR (CDCl$_3$) δ0.94 (3H, t, J=7 Hz), 1.01 (3H, d, J=7 Hz), 1.25 (H, m), 1.54 (9H, s), 1.81 (3H, s), 1.83 (H, m), 2.42 (H, d of d, J=15, 11 Hz), 2.82 (H, d, J=15 Hz), 3.72 (H, d of d, J=12, 3 Hz), 3.98 (H, m), 4.13 (H, d, J=12 Hz), 4.24 (H, d of d, J=9, 2 Hz), 4.82 (H, s), 4.88 (H, s).

Step B

Preparation of N-(tert-Butoxycarbonyl)-2(S)-[2(S)-amino-3(S)-methyl]pentyloxy-4-methyl-4-pentenoic acid The title compound was prepared in a similar fashion as that described in Example 1, Step E, but using N-(tert-butoxycarbonyl)-2(S)-methallyl-5(S)-[1(S)-methyl]propyl-2,3,5,6-tetrahydro-4H-1,4-oxazin-3-one in place of N-(tert-butoxycarbonyl)-2(S)-benzyl-5(S)-[1(S)-methyl]propyl-2,3,5,6-tetrahydro-4H-1,4-oxazin-3-one. NMR (DMSO-d$_6$) δ0.80 (3H, d, J=7 Hz), 0.83 (3H, t, J=7 Hz), 1.03 (H, m), 1.37 (9H, s), 1.51 (H, m), 1.73 (3H, s), 2.20 (H, d of d, J=15, 10 Hz), 2.37 (H, d of d, J=15, 4 Hz), 3.23 (H, d of d, J=10, 7 Hz), 3.53 (H, m), 3.72 (H, m), 4.72 (2H, s), 6.75 (H, d, J=8 Hz).

Step C

Preparation of N-(tert-Butoxycarbonyl)-2(S)-[2(S)-amino-3(S)-methyl]pentyloxy-4-methyl-4-pentenoyl-homoserine lactone The title compound was prepared in a similar fashion as that described in Example 1, Step F, but using N-(tert-butoxycarbonyl)-2S)-[2(S)-amino-3(S)-methyl]pentyloxy-4-methyl-4-pentenoic acid in place of N-(tert-butoxycarbonyl)-2(S)-[2(S)-amino-3(S)-methyl]pentyloxy-3-phenylpropionic acid. NMR (CDCl$_3$) δ0.88 (3H, t, J=7 Hz), 0.89 (3H, d, J=7 Hz), 1.13 (H, m), 1.44 (9H, s), 1.78 (3H, s), 2.31 (H, d of d, J=14, 8 Hz), 2.33 (H, m), 2.50 (H, d of d, J=15, 4 Hz), 2.65 (H, m), 3.57 (2H, d, J=7 Hz), 3.75 (H, m), 3.97 (H, d of d, J=9, 5 Hz), 4.28 (H, m), 4.48 (H, d of t, J=9, 1 Hz), 4.54 (H, d, J=9 Hz), 4.72 (H, s), 4.78 (H, s), 4.83 (H, s), 8.01 (H, m).

Step D

Preparation of N-(tert-Butoxycarbonyl)-2(S)-[2(S)-amino-3(S)-methyl]pentyloxy-4-methyl-pentanoyl-homoserine lactone A mixture of N-(tert-butoxycarbonyl)-2(S)-[2-(S)-amino-3S)-methyl]pentyloxy-4-methyl-4-pentenoyl-homoserine lactone (75 mg, 0.18 mmol) and 10% Pd/C (10 mg) in ethyl acetate (10 ml) was hydrogenated on a Parr shaker for 2 h. The catalyst was removed by filtration and the filtrate was concentrated in vacuo to afford the title compound (70 mg) as a solid. NMR (CDCl$_3$) δ0.87~0.96 (12H, m), 1.15 (H, m), 1.45 (9H, s), 1.82 (H, m), 2.32 (H, m), 2.65 (H, m), 3.52 (H, d of d, J=16, 9 Hz), 3.60 (H, d of d, J=10, 5 Hz), 3.77 (H, m), 3.85 (H, t, J=6 Hz), 4.28 (H, m), 4.48 (H, d of d, J=10, 1 Hz), 4.54 (H, d, J=12 Hz), 4.74 (H, q, J=12 Hz), 7.98 (H, d, J=8 Hz).

Step E

Preparation of 2(S)-[2(S)-Amino-3(S)-methyl]-pentyloxy-4-methylpentanoyl-homoserine lactone hydrochloride The title compound was prepared in a similar fashion as that described in Example 1, Step G, but using N-(tert-butoxycarbonyl)-2(S)-[2(S)-amino-3(S)-methyl]pentyloxy-4-methylpentanoyl-homoserine lactone in place of N-(tert-butoxycarbonyl)-2(S)-[2(S)-amino-3(S)-methyl]pentyloxy-3-phenylpropionyl-homoserine lactone.

Step F

Preparation of 2(S)-[2(S)-[2(R)-(tert-Butoxy-carbonyl)amino-3-triphenylmethylmercapto]-propylamino-3(S)-methyl]pentyloxy-4-methyl-pentanoyl-homoserine lactone The title compound was prepared in a similar fashion as that described in Example 1, Step H, but using 2(S)-[2(S)-amino-3(S)-methyl]-pentyloxy-4-methylpentanoyl-homoserine lactone hydrochloride in place of 2(S)-[2(S)-amino-3(S)-methyl]pentyloxy-3-phenylpropionyl-homoserine lactone hydrochloride. NMR (CD$_3$OD) δ0.86 (3H, d, J=7 Hz), 0.89 (3H, t, J=7 Hz), 0.91 (6H, d, J=7 Hz), 1.15 (H, m), 1.45 (9H, s), 1.80 (H, m), 2.25~2.55 (6H, m), 2.67 (H, d of d, J=12, 4 Hz), 3.60 (H, m of d, J=10 Hz), 3.65 (H, m), 3.74 (H, d of d, J=10, 5 Hz), 4.28 (H, m), 4.43 (H, d of t, J=10, 1 Hz), 4.66 (H, m), 7.2~7.45 (15H, m).

Step G

Preparation of 2(S)-[2(S)-[2(R)-Amino-3-mercapto]propylamino-3(S)-methyl]pentyloxy4-methylpentanoyl-homoserine lactone The title compound was prepared in a similar fashion as that described in Example 1, Step I, but using 2(S)-[2(S)-[2(R)-tert-butoxycarbonyl)amino-3-mercapto]propylamino-3(S)-methyl]pentyloxy-4-methyl-pentanoyl-homoserine lactone in place of 2(S)-[2(S)-[2(R)-(tert-butoxycarbonyl)amino-3-mercapto]propyl-amino-3(S)-methyl]pentyloxy-3-phenylpropionyl-homoserine lactone. NMR (CD$_3$OD) δ0.95 (3H, d, J=7 Hz), 0.97 (3H, d, J=7 Hz), 0.98 (3H, t, J=7 Hz), 1.04 (3H, d, J=7 Hz), 1.25~1.60 (3H, m), 1.65~1.9 (2H, m), 1.97 (H, m), 2.35~2.60 (2H, m), 2.92 (H, d of d, J=14, 7 Hz), 3.06 (H, d of d, J=14, 5 Hz), 3.28 (H, m), 3.38 (H, d of d, J=14, 7 Hz), 3.54 (H, d of d, J=14, 5 Hz), 3.68 (H, d of d, J=12, 4 Hz), 3.82 (H, m), 3.90 (H, d of d, J=12, 5 Hz), 4.00 (H, d of d, J=12, 6 Hz), 4.33 (H, m), 4.50 (2H, m of t, J=12 Hz). Anal. Calcd for C$_{19}$H$_{37}$N$_3$O$_4$S.2.6CF$_3$CO$_2$H.0.8H$_2$O: C, 40.68; H, 5.81; N, 5.88 Found:C, 40.68; H, 5.83; N, 6.04.

Step H

Preparation of 2(S)-[2(S)-[2(R)-Amino-3-mercapto]propylamino-3(S)-methyl]pentyloxy-4-methylpentanoyl-homoserine The title compound was prepared in a similar fashion as that described in Example 1, Step J, but using 2(S)-[2(S)-[2(R)-Amino-3-mercapto]propylamino-3(S)-methyl]

pentyloxy-4-methylpentanoyl-homoserine lactone in place of 2(S)-[2(S)-[2(R)-amino-3-mercapto]propylamino-3(S)-methyl]pentyloxy-3-phenyl-propionyl-homoserine lactone.

Example 6

Preparation of 2(S)-[2(S)-[2(R)-Amino-3-mercapto]-propylamino-3(S)-methyl]pentyloxy-3-methylbutanoyl-homoserine lactone and 2(S)-[2(S)-[2(R)-Amino-3-mercapto]propylamino-3(S)-methyl]pentyloxy-3-methyl-butanoyl-homoserine

Step A

Preparation of N-(tert-Butoxycarbonyl)-2(R)-(1-hydroxy-1-methyl) ethyl-5(S)-[1(S)-methyl]propyl-2,3,5,6-tetrahydro-4H-1,4-oxazin-3-one A solution of N-(tert-butoxycarbonyl)-5(S)-[1(S)-methyl]propyl-2,3,5,6-tetrahydro-4H-1,4-oxazin-3-one (0.5 g, 1.94 mmol) in DME (6 ml) was cooled to −60° C. and transferred under argon via a cannula to a flask containing a solution of NaHMDS (1.0M in THF, 2.14 ml, 2.14 mmol) at −78° C. The resulting mixture was stirred for 5 mins, acetone (0.16 ml, 2.14 mmol) was added and stirred at −78° C. for 4 h. The reaction mixture was treated with saturated aqueous ammonium chloride (2.14 ml), brine (4 ml) and water (1 ml). Then, it was extracted with ether (2×10 ml). The combined extracts were dried, filtered and evaporated to yield a residue. Purification of the residue by flash chromatography afforded the title compound (0.28 g, 0.88 mmol, 45%) as an oil. NMR (CDCl$_3$) δ0.93 (3H, t, J=7 Hz,), 1.00 (3H, d, J=7 Hz), 1.27 (3H, s), 1.28 (3H, s), 1.54 (9H, s), 1.82 (H, m), 3.73 (H, m), 3.8–4.0 (2H, m), 4.0–4.25 (2H, m), 4.58 (H, m).

Step B

Preparation of N-(tert-Butoxycarbonyl-2-iso-propylidenyl-5 (S)-[1(S)-methyl]-propyl-2,3,5,6-tetrahydro-4H-1,4-oxazin-3-one A solution of N-(tert-butoxycarbonyl)-2(R)-(1-hydroxy-1-methyl) ethyl-5(S)-[1(S)-methyl]propyl-2,3,5,6-tetrahydro-4H -1,4-oxazin3-one (0.597 g, 1.26 mmol) in pyridine (20 ml) was cooled to 0° C. and treated with phosphorus oxychloride (1.23 ml) and the resulting mixture was allowed to warm to room temperature and stirred overnight. The reaction mixture was treated with saturated sodium bicarbonate solution (50 ml) and extracted with methylene chloride three times. The combined extracts were washed with brine (15 ml), dried, filtered and evaporated to give a residue which was purified by flash chromatography to yield the title compound (0.196 g, 0.64 mmol, 51%). NMR (CDCl$_3$) δ0.91 (3H, t, J=7 Hz), 0.97 (3H, d, J=7 Hz), 1.20 (H, m), 1.54 (9H, s), 1.80 (3H, s), 2.14 (3H, s), 3.93 (H, d of d, J=12, 3 Hz), 4.07 (H, t of d, J=8, 2 Hz), 4.23 (H, d of d, J=12, 4 Hz).

Step C

Preparation of N-(tert-Butoxycarbonyl)-2(S)-isopropyl-5(S)-[1(S)-methyl]propyl-2,3,5,6-tetrahydro-4H-1,4-oxazin-3-one A mixture of N-(tert-butoxycarbonyl)-2-iso-propylidenyl-5(S)-[1(S)-methyl]propyl-2,3,5,6-4H-1,4-oxazin-3-one (0.19 g, 0.63 mmol) and PtO$_2$ (20 mg) in ethyl acetate (20 ml) was hydrogenated on a Parr shaker for 5 h at 54 psi. The reaction mixture was filtered through a pad of Celite and the filtrate was evaporated to give the title compound (0.188 mg, 0.63 mmol, 99%) as an oil. NMR (CDCl$_3$) δ0.92 (3H, t, J=7 Hz), 0.93 (3H, d, J=7 Hz), 0.99 (3H, d, J=7 Hz), 1.04 (3H, d, J=7 Hz), 1.53 (9H, s), 1.84 (H, m), 2.47 (H, m), 3.67 (H, d of d, J=14, 4 Hz), 3.90 (H, d, J=3 Hz), 3.92 (H, m), 4.11 (H, d, J=14 Hz).

Step D

Preparation of N-(tert-Butoxycarbonyl)-2(S)-[2(S)-amino-3(S)-methyl]pentyloxy-3-methyl-butanoic acid The title compound was prepared in a similar fashion as that described in Example 2, Step B, but using N-(tert-butoxycarbonyl)-2(S)-isopropyl-5(S)-[1(S)-methyl]propyl-2,3,5,6-tetrahydro-4H-1,4-oxazin-3-one in place of N-(tert-butoxycarbonyl)-2(S)-benzyl-2-methyl-5(S)-[1(S)-methyl]propyl-2,3,5,6-tetrahydro-4H-1,4-oxazin-3-one.

Step E

Preparation of N-(tert-butoxycarbonyl)-2(S)-[2(S)-amino-3(S)-methyl]pentyloxy-3-methyl-butanoyl-homoserine lactone The title compound was prepared in a similar fashion as that described in Example 1, Step F, but using N-(tert-butoxycarbonyl)-2(S)-[2(S)-amino-3(S)-methyl]pentyloxy-3-methylbutanoic acid in place of N-(tert-butoxycarbonyl)-2(S)-[2(S)-amino-3(S)-methyl]-pentyloxy-3-phenyl-propionic acid. NMR (CDCl$_3$) δ0.84–0.95 (9H, m), 0.99 (3H, d, J=7 Hz), 1.44 (9H, s), 2.11 (H, m), 2.34 (H, m), 2.63 (H, m), 3.50–3.65 (3H, m), 3.75 (H, m), 4.28 (H, m), 4.45–4.60 (2H, m), 4.72 (H, m), 8.05 (H, m).

Step F

Preparation of 2(S)-[2(S)-Amino-3(S)-methyl]-pentyloxy-3-methyl-butanoyl-homoserine lactone hydrochloride The title compound was prepared in a similar fashion as that described in Example 1, Step G, but using N-(tert-butoxycarbonyl)-2 (S)-[2(S)-amino-3(S)-methyl]pentyloxy-3-methylbutanoyl-homoserine lactone in place of N-(tert-butoxycarbonyl)-2(S)-[2(S)-amino-3(S)-methyl]pentyloxy-3-phenylpropionyl-homoserine lactone.

Step G

Preparation of 2(S)-[2(S)-[2(R)-(tert-Butoxy-carbonyl)amino-3-triphenylmethylmercapto]propylamino-3(S)-methyl]pentyloxy-3-methylbutanoyl-homoserine lactone The title compound was prepared in a similar fashion as that described in Example 1, Step H, but using 2(S)-[2(S)-amino-3(S)-methyl-]pentyloxy-3-methylbutanoyl-homoserine lactone hydrochloride in place of 2(S)-[2(S)-amino-3(S)-methyl]pentyloxy-3-phenylpropionyl-homoserine lactone hydrochloride.

Step H

Preparation of 2(S)-[2(S)-[2(R)-Amino-3-mercapto]propylamino-3(S)-methyl]pentyloxy-3-methylbutanoyl-homoserine lactone The title compound was prepared in a similar fashion as that described in Example 1, Step I, but using 2(S)-[2(S)-[2(R)-(tert-butoxycarbonyl)amino-3-triphenylmethylmercapto]propylamino-3(S)-methyl]pentyloxy-3-methylbutanoyl-homoserine lactone in place of 2(S)-[2(S)-[2(R)-(tert-butoxycarbonyl)amino-3-triphenylmethyl-mercapto]propylamino-3(S)-methyl]-pentyloxy-3-phenylpropionyl-homoserine lactone. NMR (CD$_3$OD) δ0.93–1.04 (9H, m), 1.07 (3H, d, J=7 Hz), 1.33 (H, m), 1.58 (H, m), 2.0 (2H, m), 2.4–2.6 (2H, m), 2.93 (H, d of d, J=16.7 Hz), 3.08 (H, d of d, J=16.5 Hz), 3.80–3.95 (2H, m), 4.35 (H, m), 4.52 (2H, t, J=10 Hz). Anal. Calcd for C$_{18}$H$_{34}$N$_3$O$_4$S.2.35CF$_3$CO$_2$H:C, 41.53; H, 5.58; N, 6.40. Found: C, 4.57; H, 5.50; N, 6.58.

Step I

Preparation of 2(S)-[2(S)-[2(R)-Amino-3-mercapto]propylamino-3(S)-methyl]pentyloxy-3-methylbutanoyl-homoserine The title compound was prepared in a similar fashion as that described in Example 1, Step J, but using 2(S)-[2(S)-[2(R)-amino-3-mercapto]-propylamino-3(S)-methyl]pentyloxy-3-methylbutanoyl-homoserine lactone in place of 2(S)-[2(S)-[2(R)-amino-3-mercapto]propylamino-3(S)-methyl]pentyloxy-3-phenyl-propionyl-homoserine lactone.

Example 7

Preparation of 2(S)-[2(S)-[2(R)-Amino-3-mercapto]-propylamino-3(S)-methyl]-pentyloxy-3-phenylbutanoylhomoserine lactone and 2(S)-[2(S)-[2(R)-Amino-3-mercapto]propylamino-3(S)-methyl]pentyloxy-3-phenylbutanoyl-homoserine Step A
Preparation of N-(tert-Butoxycarbonyl)-2(S)-(a-methylbenzyl-5(S)-[1(S)-methyl]propyl-2,3,5,6-tetrahydro-4H-1,4-oxazin-3-one A solution of N-(tert-butoxycarbonyl)-5(S)-[1-(S)-methyl]propyl-2,3,5,6-tetrahydro-4H-1,4-oxazin-3-one (1 g, 3.89 mmol) in DME (17 ml) was cooled to −63° C. and added via a cannula to a stirred solution of NaHMDS (1.0M, 4.27 ml, 4.27 mmol) in THF at −78° C. under argon. After 10 min. stirring, a-methylbenzyl bromide (2.65 ml, 19.5 mmol) was added to the mixture, then stirred at −40° C. for 2 hours. The reaction mixture was successively treated with saturated ammonium chloride (2.65 ml), brine (5 ml) and water (2 ml), then extracted with ethyl acetate twice (2×20 ml). The combined extracts were washed with brine, dried, filtered and evaporated. The residue was purified by flash chromatography to afford the title compound. NMR $(CDCl_3)$ δ0.91 (3H, t, J=7 Hz), 1.0 (3H, d, J=Hz), 1.37 (3H, d, J=7 Hz), 1.56 (9H, s), 1.78 (H, m), 3.61 (H, d of d, J=12.3 Hz), 3.70 (H, m), 3.92 (H, m) 4.09 (H, d, J=12 Hz), 4.19 (H, m), 7.2~7.4 (5H, m).

Step B
Preparation N-(tert-Butoxycarbonyl)-2(S)-[2(S)-amino-3(R)-methyl]-pentyloxy-3-phenyl-butanoic acid The title compound was prepared in a similar fashion as that described in Example 1, Step E, but using N-(tert-butoxycarbonyl)-2(S)-(a-methyl)benzyl-5(S)-[1(S)-methyl] propyl-2,3,5,6-tetrahydro-4H-1,4-oxazin-3-one in place of N-(tert-butoxycarbonyl)-2(S)-benzyl-5(S)-[1(S)-methyl] propyl-2,3,5,6-tetrahydro-4H-1,4-oxazin-3-one. NMR $(DMSO-d_6)$ δ0.73 (3H, d, J=7 Hz), 0.82 (3H, t, J=7 Hz), 1.04 (H, m), 1.17 (3H, d, J=7 Hz), 1.38 (9H, s), 7.1~7.3 (5H, m).

Step C
Preparation of N-(tert-Butoxycarbonyl)-2(S)-[2(S)-amino-3(S)-methyl]-pentyloxy-3-phenyl-butanoyl-homoserine lactone The title compound was prepared in a similar fashion as that described in Example 1, Step F, but using N-(tert-butoxycarbonyl)-2(S)-[2(S)-amino-3(S)-methyl]pentyloxy-3-phenylbutanoic acid in place of N-(tert-butoxycarbonyl)-2(S)-[2(S)-Amino-3(S)-methyl]-pentyloxy-3-phenylpropionic acid. NMR $(CDCl_3)$ δ0.77 (3H, d, J=7 Hz), 0.87 (3H, t, J=Hz), 1.08 (h, m), 1.24 (3H, d, J=7 Hz), 1.48 (9H, s), 2.31 (H, m), 2.62 (H, m), 3.13 (H, t, J=10 Hz), 3.35 (2H, m), 3.70 (H, m), 3.93 (H, m), 4.29 (H, m), 4.48 (2H, m), 4.71 (H, m), 7.3 (5H, m), 8.07 (H, m).

Step D
Preparation of 2(S)-[2(S)-Amino-3(S)-methyl]-pentyloxy-3-phenylbutanoyl-homoserine lactone hydrochloride The title compound was prepared in the same manner as that described in Example, Step G, but using N-(tert-butoxycarbonyl)-2(S)-[2(S)-Amino-3(S)-methyl]-pentyloxy-3-phenylbutanoyl-homoserine lactone in place of N-(tert-butoxycarbonyl)-2(S)-[2(S)-amino-3(S)-methyl] pentyloxy-3-phenylpropionyl-homoserine lactone. NMR $(DMSO-d_6)$ δ0.70 (3H, d, J=7 Hz), 0.83 (3H, t, J=7 Hz), 1.08 (H, m), 1.28 (3H, d, J=7 Hz), 1.44 (H, m), 1.65 (H, m), 2.1~2.3 (2H, m), 3.09 (H, m), 3.18 (H, m), 3.57 (H, m), 3.93 (H, d, J=4 Hz), 4.22 (H, m), 4.38 (H, m), 4.48 (H, m), 7.2~7.35 (5H, m), 7.90 (H, m).

Step E
Preparation of 2(S)-[2(S)-[2(R)-(tert-Butoxy-carbonyl) amino-3-triphenylmethylmercapto]propylamino-3(S)-methyl]pentyloxy-3-phenylbutanoyl-homoserine lactone The title compound was prepared in a similar fashion as that described in Example 1, Step H, but using 2(S)-[2(S)-amino-3(S)-methyl]-pentyloxy-3-phenylbutanoyl-homoserine lactone hydrochloride in place of 2(S)-[2(S)-amino-3(S)-methyl]pentyloxy-3-phenylpropionyl-homoserine lactone hydrochloride. NMR $(CDCl_3)$ δ0.71 (3H, d, J=7 Hz), 0.85 (3H, t, J=7 Hz), 1.27 (3H, d, J=7 Hz), 1.43 (9H, s), 4.25 (H, m), 4.44 (H, m), 4.62~4.80 (2H, m), 7.15~7.5 (20H, m).

Step F
Preparation of 2(S)-[2(S)-[2(R)-Amino-3-mercapto] propylamino-3(S)-methyl]pentyloxy-3-phenylbutanoyl-homoserine lactone The title compound was prepared in a similar fashion as that described in Example 1, Step I, but using 2(S)-[2(S)-[2(R)-(tert-butoxycarbonyl)amino-3-triphenylmethylmercapto]propylamino-3 (S)-methyl]-pentyloxy-3-phenylbutanoyl-homoserine lactone in place of 2(S)-[2(S)-[2(R)-(tert-butoxycarbonyl)-amino-3-triphenylmethylmercapto]propylamino-3(S)-methyl] pentyloxy-3-phenylpropionyl-homoserine lactone. NMR $(CD_3OD)$ δ1.00 (3H, t, J=7 Hz), 1.06 (3H, d, J=7 Hz), 1.40 (3H, d, J=7 Hz), 1.55 (H, m), 1.9~2.2 (3H, m), 2.93 (H, d of d, J=16.8 Hz), 3.03~3.20 (2H, m), 3.50 (H, m of d), 3.78 (H, m), 3.80~3.90 (2H, m), 3.97 (H, d, J=8 Hz), 4.12~4.30 (2H, m), 4.44 (H, d of t), 7.30 (5H, m). Anal. Calcd for $C_{23}H_{37}N_3O_4S.2.2CF_3CO_2H.1.90H_2O$: C, 44.67; H, 5.88; N, 5.70 Found: C, 44.70; H, 5.89; N, 5.58

Step G
Preparation of 2(S)-[2(S)-[2(R)-Amino-3-mercapto] propylamino-3(S)-methyl]pentyloxy-3-phenylbutanoyl-homoserine The title compound was prepared in a similar fashion as that described in Example 1, Step J, but using 2(S)-[2(S)-[2(R)-amino-3-mercapto]propylamino-3 -(S)-methyl] pentyloxy-3-phenylbutanoyl-homoserine lactone in place of 2(S)-[2(S)-[2(R)-amino-3-mercapto]propylamino-3(S)-methyl]pentyloxy-3-phenyl-propionyl homoserine lactone.

Example 8

Preparation of 2(S)-[2(S)-[2(R)-Amino-3-mercapto]-propylamino-3(S)-methyl]pentylthio-2-methyl-3-phenyl-propionyl-homoserine lactone and 2(S)-[2(S)-[2(R)-Amino-3-mercapto]propylamino-3(S)-methyl]pentylthio-2-methyl-3-phenylpropionyl-homoserine Step A
Preparation of methyl α-[3(S)-methyl-4(S)-(tert-butoxycarbonyl)amino]pentylthioacetate Boc anhydride (6.56 g, 30 mmol) was added to a stirred solution of L-isoleucinol (3.2 g, 27 mmol) in THF (70 ml). The resulting mixture was warmed but kept below 50° C. to effect a clear solution. Then, the stirring was continued at room temperature for 45 minutes. The mixture was evaporated and the residue was redissolved in chloroform (70 ml), cooled to 0° C. and treated successively with triethylamine (5.8 ml, 41 mmol) and methanesulfonyl chloride (3.2 ml, 41 mmol). The resulting mixture was stirred at room temperature for 0.5 hours, concentrated in vacuo and the residue was distributed between ethyl acetate (100 ml), and water (100 ml). The organic layer was washed with water twice (2×100 ml), dried, filtered and evaporated. The solid residue was dissolved in THF (70 ml), with cesium carbonate (8.9 g, 27 mmol) and methyl a-mercaptoacetate (2.5 ml, 27 mmol). The resulting mixture was heated at reflux for 1 hour. Additional amounts of cesium carbonate (0.9 g) and methyl mercaptoacetate (0.25 ml) were added and heating continued for another hour. After cooling, the solvent was removed by evaporation and the residue was partitioned between ethyl acetate (100 ml) and water (100 ml). The organic layer was washed with water (2×100 ml), dried, filtered and evaporated. Purification of the residue by flash chromatography using hexane:ethyl acetate (v:1=9=1) as the eluant gave the title compound (6.04 g, 19.8 mmol, 73%) as an oil. NMR (CDCl₃) δ0.90 (3H, d, J=6 Hz), 0.93 (3H, t, 3=6 Hz), 1.11 (H, m), 1.47 (9H, s), 1.60 (H, m), 3.67 (H, d of d, J=14.8 Hz), 2.77 (H, d of d, J=14.4 Hz), 3.23 (H, d, J=14 Hz), 3.33 (H, d, J=14 Hz), 3.70 (H, m), 4.60 (H, m).

Step B

Preparation of 5(S)-[1(S)-methyl]propyl-2,3,5,6-tetrahydro-4H-1,4-thiazin-3-one

Trifluoroacetic acid (8 ml) was added to a solution of methyl α-[3(S)-methyl-4(S)-(tert-butoxy-carbonyl)amino] pentylthioacetate (6.04 g, 19.8 mmol) in chloroform (10 ml). The mixture was stirred at room temperature for 3 hours, then concentrated by evaporation. The residue was treated with toluene (80 ml) and di-i-propylethylamine (10 ml), heated on a steam bath for 0.5 hours. After cooling, the reaction mixture was concentrated by evaporation and the residue was partitioned between ethyl acetate and water. The organic layer was dried, filtered and evaporated to yield the title compound (2.73 g, 15.8 mmol, 80%) as a solid, mp 103°–5° C. NMR (CDCl₃) δ0.92 (3H, d, J=6 Hz), 0.94 (3H, t, J=6 Hz), 1.25 (H, m), 1.4–1.65 (2H, m), 2.63 (H, d of d, J=14.11 Hz), 2.71 (H, d of d, J=14.4 Hz), 3.24 (H, d, J=17 Hz), 3.34 (H, d, J=17 Hz), 3.60 (H,m), 6.15 (H, bs).

Step C

Preparation of N-(tert-Butoxycarbonyl)-5(S)-[1(S)-methyl] propyl-2,3,5,6-tetrahydro-4H-1,4,-thiazin-3-one The title compound was prepared in a similar fashion as that described in Example 1, Step C, but using THF and 5(S)-[1(S)-methyl]propyl-2,3,5,6-tetrahydro-4H-1,4-thiazin-3-one in place of methylene chloride and 5(S)-[1(S)-methyl]propyl-2,3,5,6-tetrahydro-4H-1,4-oxazin-3-one, respectively. NMR (CDCl₃) δ0.92 (3H, t, J=6 Hz), 0.99 (3H, d, J=6 Hz), 1.14 (H, m), 1.58 (9H, s), 1.97 (H, m), 2.90 (H, d of d, J=13.5 Hz), 3.05 (H, d of d, J=13.5 Hz), 3.32 (H, d, J=15 Hz), 3.42 (H, d, J=15 Hz), 4.50 (H, m).

Step D

Preparation of N-(tert-Butoxycarbonyl)-2(S)-benzyl-5(S)-[1(S)-methyl]propyl-2,3,5,6-tetrahydro-4H-1,4-thiazin-3-one The title compound was prepared in a similar fashion as that described in Example 1, Step D, but using benzyl iodide and N-(tert-butoxycarbonyl)-5(S)-[1(S)-methyl]propyl-2,3,5,6-tetrahydro-4H-1,4-thiazin-3-one in place of benzyl bromide and N-tert-butoxycarbonyl)-5(S)-[1(S)-methyl]propyl-2,3,5,6-tetrahydro-4H-1,4-oxazin-3-one, respectively. NMR (CDCl₃) δ0.85 (3H, d, J=6 Hz), 0.88 (3H, t, J=6 Hz), 1.13 (H, m), 1.52 (9H, s), 1.96 (H, m), 2.72 (H, d of d, J=14.6 Hz), 3.44 (H, d of d, J=14.6 Hz), 3.83 (H, d of d, J=8.5 Hz), 4.26 (H, m), 7.3 (5H, m).

Step E

Preparation of N-(tert-butoxycarbonyl)-2(S)-benzyl-2-methyl-5(S)-[1(S)-methyl]propyl-2,3,5,6-tetrahydro-4H-1,4-thiazin-3-one Sodium bis(trimethylsilyl)amide (1M in THF, 6 ml, 6 mmol) was added to a solution of N-(tert-butoxycarbonyl)-2(S)-benzyl-5(S)-[1(S)-methyl]propyl-2,3,5,6-tetrahydro-4H-1,4-thiazin-3-one (1.85 g, 5.1 mmol) in DME (10 ml) at −78° C. under argon. The mixture was stirred at −78° C. for 15 minutes and treated with methyl iodide (0.38 ml, 6 mmol). The reaction mixture was stirred at −78° C. for 1 hour and quenched with acetic acid (1 ml). The final mixture was partitioned between ethyl acetate (100 ml) and water (100 ml). The organic layer was washed with water (2×100 ml), dried, filtered and evaporated to give a residue which was purified by flash chromatography. Elution of the column with hexane/ethyl acetate (v:v=20:1) gave the title compound (1.16 g, 3.1 mmol, 79% based on the unrecovered starting material). NMR (CDCl₃) δ0.75 (3H, d, J=6 Hz), 0.82 (3H, t, J=6 Hz), 1.05 (H, m), 1.33 (H, m), 1.51 (9H, s), 1.56 (3H, s), 1.78 (H, m), 2.56 (H, d of d, J=15.6 Hz), 2.85 (H, d of d, J=15.5 Hz), 3.03 (H, d, J=14 Hz), 3.28 (H, d, J=14 Hz), 4.23 (H, m), 7.28 (5H, m). Further elution led to the recovery of the starting material (0.44 g, 1.2 mmol).

Step F

Preparation of 2(S)-[2(S)-Amino-3(S)-methyl]-pentylthio-2-methyl-3-phenylpropionic acid hydrochloride N-(tert-Butoxycarbonyl)-2(S)-benzyl-2-methyl-5(S)-[1(S)-methyl]propyl-2,3,5,6-tetrahydro-4H-1,4-thiazin-3-one (0.96 g, 2.55 mmol) was dissolved in a mixture of acetic acid (10 ml), water (5 mL) and hydrochloric acid (12N, 5 ml). The resulting mixture was stirred and heated on a steam bath for 5 hours. After cooling, the reaction mixture was evaporated in vacuo to afford the title compound (ca. 0.75 g, 2.5 mmol). NMR (CDCl₃) δ0.96 (3H, m), 1.07 (3H, m) 1.48 (3H, s), 1.61 (H, m), 2.0 (H, m), 2.94 (H, d of d, J=14 Hz), 3.1 (2H, bs), 3.40 (H, d of d, J=14 Hz), 7.30 (5H, m).

Step G

Preparation of N-(tert-Butoxycarbonyl)-2(S)-[2(S)-amino-3(S)-methyl]pentylthio-2-methyl-3-phenylpropionic acid To a stirred solution of 2(S-[2(S)-amino-3(S)-methyl] pentylthio-2-methyl-3-phenylpropionic acid hydrochloride (ca. 0.75 g, 2.5 mmol) in THF (28 ml) and water (4 ml) were added Boc anhydride (0.87 g, 4 mmol) and triethylamine (0.5 ml). The resulting mixture was stirred at room temperature overnight. An additional portion of triethylamine (0.1 ml) was added and stirring was continued for 5 hours. The reaction mixture was partitioned between ethyl acetate and 10% citric acid. The aqueous layer was washed with water, dried, filtered and evaporated to give the title compound (ca. 0.99 g, 2.5 mmol) as a gummy oil. NMR (DMSO-d₆) δ0.82 (3H, d, J=6 Hz), 0.85 (3H, t, J=6 Hz), 1.37 (9H, s), 1.38 (3H, s), 2.67 (H, d of d, J=12, 6 Hz), 2.80 (H, d of d, J=12, 5 Hz), 2.82 (H, d, J=14 Hz,), 3.32 (H, d, J=14 Hz), 3.48 (H, m), 6.78 (H, d, J=9 Hz), 7.25 (5H, m).

Step H

Preparation of N-(tert-Butoxycarbonyl)-2(S)-[2(S)-amino-3(S)-methyl]-pentylthio-2-methyl-3-phenylpropionyl-homoserine lactone The title compound was prepared in a similar fashion as that described in Example 1, Step F, but using N-(tert-butoxycarbonyl)-2(S)-[2(S)-amino-3(S)-methyl]pentylthio-2-methyl-3-phenylpropionic acid in place of N-(tert-butoxycarbonyl)-2(S)-[2(S)-amino-3(S)-methyl]pentyloxy-3-phenylpropionic acid. NMR (CDCl₃) δ0.88 (3H, t, J=6 Hz), 0.90 (3H, d, J=6 Hz), 1.08 (H, m), 2.10 (H, m), 2.50 (H, m), 2.58 (H, d of d, J=14.11 Hz), 2.80 (H, d of d, J=12.4 Hz), 3.05 (H, d, J=14 Hz), 3.12 (H, d, J=14 Hz), 3.70 (H, m), 4.25 (H, m), 4.42 (H, m), 4.55–4.75 (2H, m), 7.25 (5H, m), 7.90 (H, d, J=8 Hz).

Step I

Preparation of 2(S)-[2(S)-Amino-3(S)methyl]-pentylthio-2-methyl-3-phenylpropionyl-homo-serine lactone hydrochloride The title compound was prepared in a similar fashion as that described in Example 1, Step G, but using N-(tert-butoxycarbonyl)-2(S)-[2(S)-amino-3(S)-methyl]pentylthio-2-methyl-3-phenylpropionyl-homoserine lactone in place of N-tert-butoxycarbonyl)-2(S)-[2(S)-amino-3(S)-methyl] pentyloxy-3-phenyl-propionyl-homoserine lactone. NMR (DMSO-d₆) δ0.88 (3H, t, J=6 Hz), 0.92 (3H, d, J=6 Hz), 1.13

(H, m), 1.39 (3H, s), 1.42 (H, m), 1.73 (H, m), 2.2~2.4 (2H, m), 3.71 (H, d of d, J=14.9 Hz), 2.90 (H, d, J=13 Hz), 2.93 (H, d of d, J=14.5 Hz), 3.25 (H, m), 3.31 (H, d, J=13 Hz), 4.25 (H, m), 4.40 (H, m), 4.62 (H, q, J=10 Hz), 7.25 (5H, m), 8.53 (H, d, J=8 Hz).

Step J

Preparation of 2(S)-[2(S)-[2(R)-(tert-Butoxy-carbonyl) amino-3-triphenylmethylmercapto]-propylamino-3(S)-methyl]pentylthio-2-methyl-3-phenylpropionyl-homoserine lactone The title compound was prepared in a similar fashion as that described in Example 1, Step H, but using 2(S)-[2(S)-amino-3(S)-methyl]pentylthio-2-methyl-3-phenylpropionyl-homoserine lactone hydrochloride. NMR (CD₃OD) δ0.81 (3H, d, J=6 Hz), 0.90 (3H, t, J=6 Hz), 1.10 (H,m), 1.30 (H, m), 1.38 (3H, s), 1.43 (9H, s), 1.60 (H, m), 2.93 (H, d, J=14 Hz), 3.21 (H, d, J=14 Hz), 3.57 (H, m), 4.25 (H, m), 4.42 (H, m), 4.45~4.65 (2H, m), 7.15~7.45 (20H, m).

Step K

Preparation of 2(S)-[2(S)-[2(R)-Amino-3-mercapto]propylamino-3(S)-methyl]pentylthio-2-methyl-3-phenylpropionyl-homoserine lactone The title compound was prepared in a similar fashion as that described in Example 1, Step I, but using 2(S)-[2(S)-[2(R)-(tert-butoxycarbonyl)-amino-3-triphenylmethylmercapto]propylamino-3(S)-methyl]pentylthio-2-methyl-3-phenylpropionyl-homoserine lactone in place of 2(S)-[2(S)-[2(R)-(tert-butoxy-carbonyl)amino-3-triphenyl methylmercapto]propyl-amino-3(S)-methyl]pentyloxy-3-phenyl-propionyl-homoserine lactone. NMR (CD₃OD) δ0.98 (3H, t, J=7 Hz), 1.01 (3H, d, J=7 Hz), 1.32 (H, m), 1.57 (3H, s), 1.87 (H, m), 2.43 (2H, m), 4.25~4.35 (2H, m), 4.53 (H, m), 7.15~7.35 (5H, m). MS m/e 468M₊.

Step L

Preparation of 2(S)-[2(S)-[2(R)-Amino-3-mercapto]propylamino-3(S)-methyl]pentylthio-2-methyl-3-phenylpropionyl-homoserine The title compound was prepared in a similar fashion as that described in Example 1, Step J, but using 2(S)-[2(S)-[2(R)-amino-3-mercapto]propylamino-3(S)-methyl]pentylthio-2-methyl-3-phenyl-propionyl-homoserine lactone in place of 2(S)-[2(S)-[2(R)-amino-3-mercapto]propylamino-3(S)-methyl]pentyloxy-3-phenyl-propionyl-homoserine lactone.

Example 9

Preparation of 2(S)-[2(S)-[2(R)-Amino-3-mercapto]-propylamino-3(S)-methyl]-pentylsulfonyl-2-methyl-3-phenylpropionyl-homoserine lactone and 2(S)-[2(S)-[2(R)-Amino-3-mercapto]propylamino-3(S)-methyl]pentyl-sulfonyl-2-methyl-3-phenylpropionyl-homoserine Step A Preparation of N-(tert-Butoxycarbonyl)-2(S)-[2(S)-amino-3(S)-methyl]pentylsulfonyl-2-methyl-3-phenylpropionyl-homoserine lactone To a solution of N-(tert-butoxycarbonyl)-2(S)-2(S)-amino-3(S)-methyl]pentylthio-2-methyl-3-phenylpropionyl-homoserine lactone (0.39 g, 0.82 mmol) in chloroform (5 ml) was added a solution of m-chloropeoxybenzoic acid (0.3 g, 1.7 mmol) in chloroform (5 ml). The resulting mixture was stirred at room temperature until the completion of the reaction was indicated by TLC analysis. The reaction mixture was diluted with ethyl acetate (100 ml), then washed with saturated sodium bicarbonate (3×50 ml) followed by water (2×50 ml). The organic layer was dried, filtered and evaporated to give the title compound (0.37 g, 0.72 mmol, 88%) as a gum. NMR (CDCl₃) δ0.92 (3H, t, J=7 Hz), 0.94 (3H, d, J=7 Hz), 1.46 (9H, s), 1.51 (3H, s), 1.87 (H, m), 2.34 (H, m), 2.68 (H, m), 3.17 (H, d, J=14 Hz), 3.63 (H, d, J=14Hz), 4.16 (H, m), 4.32 (H, m), 4.5~4.65 (2H, m), 5.00 (H, d, J=10 Hz), 7.15~7.35 (5H, m). FABMS m/e 511 (M+H⁺).

Step B

Preparation of 2(S)-[2(S)-Amino-3(S)-methyl]-pentylsulfonyl-2-methyl-3-phenylpropionyl-homoserine lactone hydrochloride The title compound was prepared in a similar fashion as that described in Example 1, Step G, but using N-(tert-butoxycarbonyl)-2(S)-[2(S)-amino-3(S)-methyl]pentylsulfonyl-2-methyl-3-phenyl-propionyl-homoserine lactone in place of N-(tert-butoxy-carbonyl)-2(S)-[2(S)-amino-3(S)-methyl]pentyloxy-3-phenylpropionyl-homoserine lactone. NMR (DMSO-d₆) δ0.88 (3H, t, J=7 Hz), 0.94 (3H, d, J=7 Hz), 1.42 (3H, s), 2.25~2.45 (2H, m), 2.97 (H, d, J=12 Hz), 3.65~3.80 (3H, m), 4.27 (H, m), 4.43 (H, m), 4.68 (H, d, of d, J=1 8, 10 Hz), 7.28 (5H, m), 8.80 (H, d, J=8 Hz).

Step C

Preparation of 2(S)-[2(S)-[2(R)-(tert-Butoxy-carbonyl) amino-3-triphenylmethylmercapto]-propylamino-3(S)-methyl]pentylsulfonyl-2-methyl-3-phenylpropionyl-homoserine lactone The title compound was prepared in a similar fashion as that described in Example 1, Step H, but using 2(S)-[2(S)-amino-3(S)-methyl]pentylsulfonyl-2-methyl-3-phenylpropionyl-homoserine lactone hydrochloride in place of 2(S)-[2(S)-amino-3(S)-methyl]pentyloxy-3-phenylpropionyl-homoserine lactone hydrochloride. NMR (CDCl₃) δ0.79 (3H, d, J=7 Hz), 0.90 (3H, t, 3=7 Hz), 1.40 (9H, s), 1.51 (3H, 1.64 (H, m), 2.95~3.22 (4H, m), 3.50~3.65 (2H, m) 4.23 (H, m), 4.46 (H, t, J=9 Hz), 4.61 (H, m), 5.08 (H, m), 7.13~7.50 (20H, m).

Step D

Preparation of 2(S)-[2(S)-[2(R)-Amino-3-mercapto]propylamino-3(S)-methyl]pentyl-sulfonyl-2-methyl-3-phenylpropionyl-homoserine lactone The title compound was prepared in a similar fashion as that described in Example 1, Step I, but using 2(S)-[2(S)-[2(R)-(tert-butoxycarbonyl)amino-3-triphenylmethylmercapto]propylamino-3(S)-methyl]-pentylsulfonyl-2-methyl-3-phenylpropionyl-homoserine lactone in place of 2(S)-[2(S)-[2(R)-(tert-butoxy-carbonyl) amino-3-triphenylmethylmercapto]propylamino-3(S)-methyl]-pentyloxy-3-phenylpropionyl-homoserine lactone. NMR (CD₃OD) δ0.97 (3H, d, J=7 Hz), 1.00 (3H, t, J=7 Hz), 1.29 (H, m), 1.49 (3H, s), 1.85 (H, m), 2.35~2.52 (2H, m), 2.76 (H, d of d, J=14.6 Hz), 3.86 (H, d of d, J=14.5 Hz), 3.00 (H, d, J=12 Hz), 3.09 (H, d of d, J=14, 5 Hz), 3.63 (H, m), 3.81 (H, d, J=12 Hz), 4.25~4.40 (2H, m), 4.53 (H, m of t), 7.20~7.35 (5H, m). Anal. Calcd for C₂₃H₃₈N₃O₅S₂.2.45 CF₃CO₂H.0.55 H₂O: C, 42.42; H, 5.31; N, 5.31. Found:C, 42.38; H, 5.28; N, 5.47.

Step E

Preparation of 2(S)-[2(S)-[2(R)-Amino-3-mercapto]propylamino-3(S)-methyl]pentyl-sulfonyl-2-methyl-3-phenylpropionyl-homo-serine The title compound was prepared in a similar fashion as that described in Example 1, Step J, but using 2(S)-[2(S)-[2(R)-amino-3-mercapto]-propylamino-3(S)-methyl]pentylsulfonyl-2-methyl-3-phenylpropionyl-homoserine lactone in place of 2(S)-[2(S)-[2(R)-amino-3-mercapto]-propylamino-3(S)-methyl]-pentyloxy-3-phenylpropionyl-homoserine lactone.

Example 10

Preparation of 2(S)-[2(R)-Amino-3-mercapto]propyl-amino-3(S)-methyl]pentyloxy-3-phenylpropionyl-methionine methyl ester

Step A

Preparation of N-(tert-Butoxycarbonyl)-2(S)-[2(S)-amino-3(S)-methyl]-pentyloxy-3-phenyl-propionyl-methione methyl ester The title compound was prepared in accordance with the procedure described in Example 1 Step F, employing methionine methyl ester hydrochloride in place of homoserine lactone hydrochloride. NMR (CD$_3$OD) δ0.78 (3H, d, J=6 Hz), 0.89 (3H, t, J=6 Hz), 1.11 (H, m), 1.47 (9H, s), 2.06 (3H, s), 2.2~2.4 (2H, m), 2.90 (H, d of d, J=14.7 Hz), 3.05 (H, d of d, J=14.5 Hz), 3.38 (H, d of d, J=8.6 Hz), 3.5~3.55 (2H, m), 3.71 (3H, s), 3.97 (H, d of d, J=7.5 Hz), 6.60 (H, d, J=10 Hz), 7.24 (5H, m).

Step B

Preparation of 2(S)-[2(S)-Amino-3(S)-methyl]-pentyloxy-3-phenylpropionyl-methionine methyl ester hydrochloride The title compound was prepared in a similar fashion as that described in Example 1, Step G, but using N-(tert-butoxycarbonyl-2(S)-[2(S)-amino-3(S)-methyl]pentyloxy-3-phenylpropionyl-methione methyl ester in place of N-(tert-butoxycarbonyl)-2(S)-[2(S)-amino-3(S)methyl]pentloxy-3-phenylpropionyl-homoserine lactone. NMR (CD$_3$OD) δ0.84 (3H, d, J=6 Hz), 0.93 (3H, t, J=6 Hz), 1.20 (H, m), 1.40 (H, m), 1.60 (H, m), 2.08 (3H, s), 2.3~2.5 (2H, m), 2.98 (H, d of d, J=14.7 Hz), 3.11 (H, d of d, J=14.5 Hz), 3.23 (H, m), 3.57 (H, d of d, J=10.6 Hz), 3.70 (H, d, J=3 Hz), 3.73 (3H, s), 4.12 (H, d of d, J=8.6 Hz), 7.30 (5H, m).

Step C

Preparation of 2(S)-[2(S)-[2(R)-(tert-Butoxy-carbonyl)-3-triphenylmethyl-mercapto]propyl-amino-3(S)-methyl]pentyloxy-3-phenylpropionyl-methionine methyl ester The title compound was prepared in a similar fashion as that described in Example 1, Step H, but using 2(S)-[2(S)-amino-3(S)-methyl]pentyloxy-3-phenyl-propionyl-methionine methyl ester hydrochloride in place of 2(S)-[2(S)-amino-3(S)-methyl]pentyloxy-3-phenylpropionyl-homoserine lactone hydrochloride. NMR (CD$_3$OD) δ0.68 (3H, d, J=6 Hz), 0.87 (3H, t, J=6 Hz), 1.46 (9H, s), 2.05 (3H, s), 2.68 (H, m), 2.87 (H, d of d, J=14.7 Hz) 3.05 (H, d of d, J=14.4 Hz), 3.67 (3H, s), 3.91 (H, d of d, J=8.4 Hz), 4.70 (H, m), 7.1~7.4 (20H, m).

Step D

Preparation of 2(S)-[2(S)-[2(R)-Amino-3-mercapto]propylamino-3(S)-methyl]pentyloxy-3-phenylpropionyl-methionine methyl ester The title compound was prepared in the same manner as that described in Example 1, Step I, but using 2(S)-[2(S)-[2(R)-(tert-butoxycarbonyl)amino-3-triphenylmethylmercapto]propylamino-3(S)-methyl]pentyloxy-3-phenylpropionyl-methionine methyl ester in place of 2(S)-[2(S)-[2(R)-(tert-butoxycarbonyl)-amino-3-triphenylmethylmercapto]propylamino-3(S)-methyl]pentyloxy-3-phenylpropionyl-homoserine lactone. NMR (CD$_3$OD) δ0.83 (3H, d, J=6 Hz), 0.92 (3H, t, J=6 Hz), 1.20 (H, m), 1.48 (H, m), 1.84 (H, m), 2.08 (3H, s), 2.4~2.6 (2H, m), 2.8~3.0 (3H, m), 3.05~3.2 (2H, m), 3.55 (H, d of d, J=14, 4 Hz), 3.68 (2H, m), 3.73 (3H, s), 4.19 (H, d of d, J=8.6Hz), 4.68 (H, d of d, J=10.6 Hz), 7.30 (5H, m). Anal. Calcd for C$_{24}$H$_{41}$N$_3$O$_4$S$_2$.2CF$_3$CO$_2$H.0.7H$_2$O: C, 45.42; H, 6.04; N, 5.68. Found: C, 45.14; H, 5.65; N, 5.87.

Example 11

Preparation of 2(S)-[2(S)-[2(R)-Amino-3-mercapto]-propylamino-3(S)-methyl]pentyloxy-3-phenylpropionyl-methionine

Step A

Preparation of 2(S)-[2(S)-[2(R)-(tert-butoxy-carbonyl)amino-3-triphenyl-methylmercapto]-propylamino-3(S)-methyl]pentyloxy-3-phenyl-propionyl-methionine To a solution of 2(S)-[2(S)-[2(R)-(tert-butoxycarbonyl)amino-3-triphenylmethylmercapto]-propylamino -3(S)-methyl]-pentyloxy-3-phenylpropionyl-methionine methyl ester (120 mg, 0.143 mmol) in methanol (4 ml) was added sodium hydroxide (1N, 0.57 ml, 0.57 mmol) and the resulting mixture was stirred at room temperature for 3 hours. Another portion of sodium hydroxide (1N, 0.25 ml) was added and stirring continued for 0.5 hours. The reaction mixture was concentrated and the residue was dissolved in a minimum amount of water and neutralized with hydrochloric acid (1N, 0.87 ml). The aqueous solution was extracted with ethyl acetate three times. The combined extracts were dried (Na2SO4) and concentrated to yield the title compound (110 mg, 0.133 mmol, 93%). NMR (CD$_3$OD) δ0.70 (3H, d, J=6 Hz), 0.80 (3H, t, J=6 Hz), 1.05 (H, m), 1.34 (9H, s), 1.60 (H, m), 1.95 (3H, S), 2.7~2.9 (3H, m), 2.95~3.1 (2H, m), 3.95 (H, d of d, J=8, 4 Hz), 4.27 (H, d of d, J=8.6 Hz), 7.1~7.4 (20H, m).

Step B

Preparation of 2(S)-[2(S)-[2(R)-Amino-3-mercapto]propylamino-3(S)-methyl]pentyloxy-3-phenylpropionyl-methionine.

The title compound was prepared in the same manner as that described in Example 1, Step I, but using 2(S)-[2(S)-[2(R)-(tert-butoxycarbonyl)amino-3-triphenylmethylmercapto]propylamino -3(S)-methyl]pentyloxy-3-phenylpropionyl-methionine in place of 2(S)-[2(S)-[2(R)-(tert-butoxycarbonyl)-amino-3-triphenylmethylmercapto]propylamino-3(S)-methyl]-pentyloxy-3-phenylpropionyl-homoserine lactone. NMR (CD$_3$OD) δ0.82 (3H, d, J=6 Hz), 0.95 (3H, t, J=6 Hz), 1.20 (H, m), 1.40 (H, m), 1.85 (H, m), 2.10 (3H, s), 2.4~2.6 (2H, m), 3.1~3.2 (2H, m), 3.35 (H, d of d, J=14, 6 Hz), 3.55 (H, d of d, J=14, 5 Hz), 4.20 (H, d of d, J=10, 5 Hz), 4.63 (H, d of d, J=10.6 Hz), 7.27 (5H, m).

Anal. Calcd for C$_{23}$H$_{39}$N$_3$O$_4$S$_2$.2CF$_3$CO$_2$H.2H$_2$O: C, 43.25; H, 6.05; N, 5.60. Found:C, 43.09; H, 6.01; N, 5.46.

Example 12

Preparation of 2(S)-[2(S)-[2(R)-Amino-3-mercapto]-propylamino-3(S)-methyl]pentyloxy-3-phenylpropionyl-methionine sulfone methyl ester

Step A

Preparation of Methionine sulfone methyl ester

Thionyl chloride (2.63 ml, 36 mmol) was added dropwise to a stirred solution of N-Boc-Met sulfone (5 g, 18 mmol) in methanol (40 ml) cooled at 0° C. After the completion of the addition, the resulting mixture was warmed to room temperature and stirred overnight. The reaction mixture was recooled to 0° C. and slowly treated with solid sodium bicarbonate to adjust the pH to 7. The mixture was concentrated in vacuo to remove methanol and the residue was dissolved in a minimum amount of water (solution pH ca. 10) and extracted with ethyl acetate four times. The combined extracts were dried (Na$_2$SO$_4$) and concentrated to give the title compound (1.5 g). NMR (CD$_3$OD) δ2.04 (H, m), 2.21 (H, m), 2.98 (3H, s), 3.23 (2H, t, J=7 Hz), 3.63 (H, d of d, J=8.6 Hz), 3.77 (3H, s).

Step B

Preparation of N-(tert-Butoxycarbonyl)-2(S)-[2(S)-amino-3(S)-methyl]-pentyloxy-3-phenyl-propionyl-methionine sulfone methyl ester The title compound was prepared in the same fashion as that described in Example 1, Step F, but using methionine sulfone methyl ester in place of homoserine lactone hydrochloride. NMR (CD$_3$OD) δ0.80 (3H, d, J=6 Hz), 0.88 (3H, t, J=6 Hz), 1.12 (H, m), 1.47 (9H, s), 2.10 (H, m), 2.32 (H, m), 2.93 (3H, s), 3.5–3.7 (2H, m), 3.74 (3H, s), 4.01 (H, d of d, J=7.4 Hz), 4.60 (H, d of d, J=9.5 Hz), 6.60 (H, d, J=8 Hz), 7.25 (5H, m).

Step C

Preparation of 2(S)-[2(S)-Amino-3(S)-methyl]-pentyloxy-3-phenylpropionyl-methionine sulfone methyl ester hydrochloride The title compound was prepared in the same fashion as that described in Example 1, Step G, but using N-(tert-butoxycarbonyl)-2(S)-[2(S)-amino-3(S)-methyl]pentyloxy-3-phenylpropionyl-methionine sulfone methyl ester in place of N-(tert-butoxycarbonyl)-2(S)-[2(S)-amino-3(S)-methyl] pentyloxy-3-phenylpropionyl-homoserine lactone.

NMR (CD$_3$OD) δ0.85 (3H, d, J=6 Hz), 0.94 (3H, t, J=6 Hz), 1.20 (H, m), 1.52 (H, m), 1.72 (H, m), 2.14 (H, m), 2.38 (H, m), 2.98 (3H, s), 3.57 (H, d of d, J=12, 6 Hz), 3.73 (H, d of d, J=12, 9 Hz), 3.78 (3H, s), 4.15 (H, d of d, J=8.6 Hz), 4.63 (H, d of d, J=8.5 Hz), 7.30 (5H, m).

Step D

Preparation of 2(S)-[2(S)-[2(R)-(tert-Butoxy-carbonyl) amino-3-triphenylmethylmercapto]-propylamino-3(S)-methyl]pentyloxy-3-phenyl-propionyl-methionine sulfone methyl ester The title compound was prepared in a similar fashion as that described in Example 1, Step H, but using 2(S)-[2(S)-amino-3(S)-methyl]pentyloxy-3-phenyl-propionyl-methionine sulfone methyl ester hydrochloride in place of 2(S)-[2(S)-amino-3(S)-methyl]pentyloxy-3-phenylpropionyl-homoserine lactone hydrochloride. NMR (CD$_3$OD) δ0.70 (3H, d, J=6 Hz), 0.88 (3H, t, J=6 Hz), 1.10 (H, m), 1.47 (9H, s), 2.15 (H, m), 2.67 (H, m), 2.92 (3H, s), 3.67 (H, m), 4.68 (H, d of d, J=10, 6 Hz), 7.15–7.45 (20H, m).

Step E

Preparation of 2(S)-[2(S)-[2(R)-Amino-3-mercapto] propylamino-3(S)-methyl]pentyloxy-3-phenylpropionyl-methionine sulfone methyl ester The title compound was prepared in a similar fashion as that described in Example 1, Step I, but using 2(S)-[2(S)-[2(R)-(tert-butoxycarbonyl) amino-3-triphenylmethylmercapto]propylamino-3(S)-methyl] pentyloxy-3-phenylpropionyl-methionine sulfone methyl ester in place of 2(S)-[2(S)-[2(R)-(tert-butoxy-carbonyl)-amino-3-triphenylmethylmercapto]propylamino-3(S)-methyl]pentyloxy-3-phenylpropionyl-homoserine lactone. NMR (CD$_3$OD) δ0.83 (3H, d, J=6 Hz), 0.93 (3H, t, J=6 Hz), 1.20 (H, m), 1.51 (H, m), 1.80 (H, m), 2.22 (H, m), 2.43 (H, m), 3.00 (3H, s), 3.78 (3H, s), 4.20 (H, d of d, J=8.4 Hz), 4.72 (H, d of d, J=10, 6 Hz), 7.30 (5H, m). FABMS m/z 532 (MH$^+$).

Example 13

Preparation of 2(S)-[2(S)-[2(R)-Amino-3-mercapto]-propylamino-3(S)-methyl]pentyloxy-3-phenylpropionyl-methionine sulfone Step A Preparation of 2(S)-[2(S)-[2(R)-(tert-Butoxy-carbonyl) amino-3-triphenylmethylmercapto]-propylamino-3(S)-methyl]pentyloxy-3-phenyl-propionyl-methionine sulfone The title compound was prepared in a similar fashion as that described in Example 11, Step A, but using 2(S)-[2(S)-[2(R)-(tert-butoxycarbonyl)amino-3-triphenylmethylmercapto]propylamino-3 (S)-methyl]pentyloxy-3-phenylpropionyl-methionine sulfone methyl ester in place of 2(S)-[2(S)-[2(R)-(tert-butoxycarbonyl)amino-3-triphenylmethylmercapto]propylamino-3(S)-methyl]pentyloxy-methionine methyl ester. NMR (CD$_3$OD) δ0.79 (3H, d, J=6 Hz), 0.90 (3H, t, J=6 Hz), 1.47 (9H, s), 2.92 (3H, s), 4.08 (H, m), 4.32 (H, m), 7.15–7.35 (20H, m).

Step B

Preparation of 2(S)-[2(S)-[2(R)-Amino-3-mercapto] propylamino-3(S)-methyl]-pentyloxy-3-phenylpropionyl-methionine sulfone The title compound was prepared in a similar fashion as that described in Example 1, Step I, but using 2(S)-[2(S)-[2(R)-(tert-butoxycarbonyl) amino-triphenylmethylmercapto]propylamino-3(S)-methyl] pentyloxy-3-phenylpropionyl-methionine sulfone in place of 2(S)-[2(S)-[2(R)-(tert-butoxycarbonyl)amino-3-triphenylmethylmercapto]propylamino-3(S)-methyl]-pentyloxy-3-phenylpropionyl-3(S)-methyl]pentyloxy-3-phenylpropionyl-homoserine lactone. NMR (CD$_3$OD) δ0.84 (3H, d, J=6 Hz), 0.94 (3H, t, J=6 Hz), 1.21 (H, m), 1.50 (H, m), 1.82 (H, m), 2.24 (H, m), 2.47 (H, m), 2.98 (3H, s), 3.6–3.75 (3H, m), 4.20 (H, d of d, J=9.5 Hz), 4.64 (H, d of d, J=9.6 Hz), 7.30 (5H, m). Anal. Calcd for C$_{23}$H$_{39}$N$_3$O$_6$S$_2$.3CF$_3$CO$_2$H: C, 40.51; H, 4.92; N, 4.89. Found:C, 40.47; H, 5.11; N, 4.56.

Example 14

Preparation of 2(S)-[2(S)-[2(R)-Amino-3-mercapto]-propylamino-3(S)-methyl]pentyloxy-3-phenylpropionyl-methionine sulfone isopropyl ester The title compound was prepared using methods A-E from Example 12, except for Method A. Methionine sulfone isopropyl ester was prepared by coupling t-butyloxycarbonylmethionine sulfone with isopropyl alcohol using dicyclohexylcarbodiimide (DCC) and 4-dimethylaminopyridine (DMAP) followed by deprotection with HCl in EtOAc. NMR (CD$_3$OD) δ0.83 (3H, d, J=6 Hz), 0.94 (3H, t, J=6 Hz), 1.11–1.56 (2H, m), 1.28 (6H, d, J=6 Hz), 1.8–1.96 (1H, m), 2.12–2.27 (1H, m), 2.89–3.0 (2H, m), 3.01 (3H, s), 3.06–3.3 (4H, m), 3.42 (1H, dd, J=6,13 Hz), 3.65 (1H, dd, J=6, 13 Hz), 3.68–3.91 (3H, m), 4.2–4.27 (1H, m), 4.61–4.7 (1H, m), 4.96–5.12 (2H, m), 7.19–7.44 (5H, m). Anal. Calc'd. for C$_{26}$H$_{45}$N$_3$O$_6$S$_2$.2CF$_3$CO$_2$H: C, 44.07; H, 5.67; N, 4.97; Found C, 44.35; H, 5.68; N, 5.23

Example 15

Preparation of 2-(S)-[2(S)-2(R)-amino-3-mercapto]-propylamino-3(S)-methyl]pentyloxy-3-naphth-2-yl-propionyl-methionine sulfone methyl ester The title compound was prepared in similar fashion as that described in Example 12 Step E using 2-(S)-[2(S)-2(R)-(tert Butyoxycarbonyl)amino-3-triphenylmethylmercapto]-propylamino-3(S)-methyl]pentyloxy-3-naphth-2-yl-propionyl-methionine sulfone methyl ester in place of 2-(S)-[2(S)-2(R)-(tert Butyoxy-carbonyl)amino-3-triphenylmethylmercapto]-propylamino-3(S)-methyl] pentyloxy- 3-phenyl-propionyl-methionine sulfone methyl ester. NMR(CD$_3$OD) δ0.77 (3H, m), 0.85 (3H, m), 1.15 (1H, m), 1.42 (1H, m), 1.87 (1H, m), 2.23 (1H, m), 2.44 (1H, m), 2.86 (2H, m), 2.90 (3H, s), 3.12 (2H, m), 3.20–3.40 (1H, m), 3.42 (1H, m), 3.58 (1H, brd, J=14.0 Hz), 3.65–3.85 (6H,m), 4.33 (1H, m), 4.70 (1H, m), 7.40–7.50 (3H, m), 7.70–7.90 (4H, m).

Anal. Calc'd. for C$_{28}$H$_{43}$O$_6$N$_3$S$_2$% C, 41.79 H, 4.98; N, 4.19 Found % C, 41.78; H, 4.99; N, 4.27 Includes 1.55 H$_2$O and 3.45 TFA

Example 16

Preparation of 2-(S)-[2(S)-2(R)-amino-3-mercapto]-propylamino-3(S)-methyl]pentyloxy-3-naphth-2-yl-propionyl-methionine sulfone The title compound was prepared in similar fashion as that described in Example 13 Step B using 2-(S)-[2(S)-2(R)-(tert Butyoxy-carbonyl)amino-3-triphenylmethylmercapto]-propylamino-3(S)-methyl]pentyloxy-3-naphth-2-yl-propionyl-methionine sulfone in place of 2-(S)-[2(S)-2(R)-(tert Butyoxy-carbonyl)amino-3-triphenylmethylmercapto]-propylamino-3(S)-methyl]pentyloxy-3-phenyl-propionyl-methionine sulfone. NMR(CD$_3$OD) δ0.77 (3H, d, J=6.9 Hz), 0.85 (3H, t, J=7 Hz), 1.15 (1H, m), 1.45 (1H, m), 1.87 (1H, m), 2.23 (1H, m), 2.48 (1H, m), 2.86 (2H, t, J=5.6 Hz), 2.92 (3H, s), 3.14 (2H, t, J=6.8 Hz), 3.22 (1H, m), 3.38 (1H, dd, J=7.8 and 13.8 Hz), 3.58 (1H, dd, J=4.1 and 13.8 Hz), 3.65–3.85 (3H, m), 4.33 (1H, dd, J=4.6 and 5.8 Hz), 4.65 (1H, dd, J=4.68 and 9.0 Hz), 7.40–7.50 (3H, m), 7.70–7.90 (4H, m). Anal. Calc'd. for C$_{27}$H$_{41}$O$_6$N$_3$S$_2$% C, 40.11 H, 4.66; N, 4.03 Found % C, 40.11; H, 4.64; N, 4.35 Includes 1.65 H$_2$O and 3.90 TFA

Example 17

Preparation of 2-(S)-[2(S)-2(R)-amino-3-mercapto]-propylamino-3(S)-methyl]pentyloxy-3-naphth-1-yl-propionyl-methionine sulfone methyl ester The title compound was prepared in similar fashion as that described in Example 12 Step E using 2-(S)-[2(S)-2(R)-(tert Butyoxy-carbonyl)amino-3-triphenylmethylmercapto]-propylamino-3(S)-methyl]pentyloxy-3-naphth-1-yl-propionyl-methionine sulfone methyl ester in place of 2-(S)-[2(S)-2(R)-(tert Butyoxy-carbonyl)amino-3-triphenylmethylmercapto]-propylamino-3(S)-methyl]pentyloxy-3-phenyl-propionyl-methionine sulfone methyl ester. NMR(CD$_3$OD) 0.64 (3H, d, J=6.8 Hz), 0.87 (3H, t, J=7.2 Hz), 1.10 (1H, m), 1.43 (1H, m), 1.73 (1H, m), 2.24 (1H, m), 2.45 (1H, m), 2.92 (2H, dd, J=4.5 and 6.0 Hz), 2.99 (3H, s), 3.15 (2H, t, J=7.5 Hz), 3.35–3.90 (6H, m), 4.36 (1H, dd, J=8.5 and 5.3 Hz), 4.70 (1H, dd, J=5.2 and 8.9 Hz), 7.40–7.60 (4H, m), 7.80 (1H, dd, J=7.6 and 1.8 Hz), 7.90 (1H, dd, J=8.2 and 1.8 Hz), 8.19 (1H, d, J=8.3 Hz).

Anal. Calc'd. for C$_{28}$H$_{43}$O$_6$N$_3$S$_2$% C, 43.23 H, 5.15; N, 4.45 Found % C, 43.22; H, 4.80; N, 4.41 Includes 1.15 H$_2$O and 3.0 TFA

Example 18

Preparation of 2-(S)-[2(S)-2(R)-amino-3-mercapto]-propylamino-3(S)-methyl]pentyloxy-3-naphth-1-yl-propionyl-methionine sulfone The title compound was prepared in similar fashion as that described in Example 13 Step B using 2-(S)-[2(S)-2(R)-(tert Butyoxy-carbonyl)amino-3-triphenylmethylmercapto]-propylamino-3(S)-methyl]pentyloxy-3-naphth-1-yl-propionyl-methionine sulfone in place of 2-(S)-[2(S)-2(R)-(tert Butyoxy-carbonyl)amino-3-triphenylmethylmercapto]-propylamino-3(S)-methyl]pentyloxy-3-phenyl-propionyl-methionine sulfone. NMR(CD$_3$OD) δ0.64 (3H, d, J=6.9 Hz), 0.87 (3H, t, J=7.3 Hz), 1.10 (1H, m), 1.45 (1H, m), 1.75 (1H, m), 2.28 (1H, m), 2.51 (1H, m), 2.86–3.0 (2H, m), 3.32 (3H, s), 3.19 (2H, t, J=7.4 Hz), 3.35–3.65 (4H, m), 3.73 (1H, dd, J=11.5 and 2.7 Hz), 3.83 (1H, m), 4.36 (1H, dd, J=2.2 and 5.1 Hz), 4.65 (1H, dd, J=4.90 and 8.6 Hz), 7.40–7.70 (4H, m), 7.81 (1H, d, J=7.6 Hz), 7.91 (1H, d, J=7.6 Hz), 8.21 (1H, d, J=8.3 Hz).

Anal. Calc'd. for C$_{27}$H$_{41}$O$_6$N$_3$S$_2$% C, 43.23 H, 5.615 N, 4.45 Found % C, 43.22; H, 4.80; N, 4.41 Includes 0.65 H$_2$O and 2.90 TFA.

Example 19

2(S)-[2(S)-[2(R)-Amino-3-mercapto]propylamino-3(S)-methyl]pentyloxy-3-methylbutanoyl-methionine methyl ester The title compound was prepared in similar fashion as that described in Example 13 Step B using 2-(S)-[2(S)-2(R)-(tert Butyoxy-carbonyl) amino-3-triphenylmethylmercapto]-propylamino-3(S)-methyl] pentyloxy-3-methylbutanoyl-methionine methyl ester in place of 2-(S)-[2(S)-2(R)-(tert Butyoxy-carbonyl)amino-3-triphenylmethylmercapto]-propylamino-3(S)-methyl] pentyloxy-3-phenyl-propionyl-methionine methyl ester. NMR(CD$_3$OD) δ0.90–1.10 (12H, m), 1.35 (1H, m), 1.57 (1H, m), 1.90 (1H, m), 2.05 (1H, m), 2.10 (3H, s), 2.20 (1H, m), 2.50–2.70 (2H, m), 2.90–3.00 (2H, m), 3.50–3.90 (7H, m), 4.71 (1H, dd, J=3.6 and 4.9 Hz).

Anal. Calc'd. for C$_{20}$H$_{41}$O$_4$N$_3$S$_2$% C, 41.08H, 6.21; N, 5.87 Found % C, 41.08; H,6.22; N, 5.83 Includes 0.45 H20 and 2.25 TFA

Example 20

2-(S)-[2(S)-[2(R)-Amino-3-mercapto]propylamino-3(S)-methyl]pentyloxy-3-methylbutanoyl-methionine The title compound was prepared in similar fashion as that described in Example 13 Step B using 2-(S)-[2(S)-2(R)-(tert Butyoxy-carbonyl) amino-3-triphenylmethylmercapto]-propylamino-3(S)-methyl] pentyloxy-3-methylbutanoyl-methionine in place of 2-(S)-[2(S)-2(R)-(tert Butyoxy-carbonyl)amino-3-triphenylmethylmercapto]propylamino-3(S)-methyl] pentyloxy-3-phenyl-propionyl-methionine. NMR (CD$_3$OD) δ0.90–1.10 (12H, m), 1.30 (1H, m), 1.57 (1H, m), 1.90 (1H, m), 2.05 (1H, m), 2.10 (3H, s), 2.20 (1H, m), 2.50–2.70 (2H, m), 3.00–3.10 (2H, m), 3.40–3.50 (1H, m), 3.60–3.70 (2H, m), 3.75 (1H, m), 3.88 (1H, m), 4.60 (1H, dd, J=9.5 and 4.4 Hz).

Anal. Calc'd. for C$_{19}$H$_{39}$O$_4$N$_3$S$_2$% C, 40.35H, 6.09; N, 6.03 Found % C, 40.36; H,6.10; N,6.21 Includes 0.45 H$_2$O and 2.2 TFA

Example 21

Disulphide of 2(S)-[2(S)-[2(R)-Amino-3-mercapto]propylamino-3(S)-methyl]pentyloxy-3-phenylpropionyl-homoserine lactone To a solution of 2(S)-[2(S)-[2(R)-Amino-3-mercapto]propylamino-3(S)-methyl]pentyloxy-3-phenylpropionyl-homoserine lactone (87.8 mg 0.122 mmol) in methanol (12.2 ml), was added iodine, (28.7 mg, 0.131 mmol) after 15 minutes of the crude reaction mixture (4.0 ml) was purified directly by HPLC using a gradient elution 95:5 to 5:95% water:acetonitrile containing 0.1% trifluoroacetic acid, to afford the title compound. NMR(CD$_3$OD) δ0.68 (3H, d, J=6.8 Hz), 0.92 (3H, t, J=7.3 Hz), 1.10 (1H, m), 1.15 (2H, m), 1.50 (1H, m), 1.80 (1H, m), 2.17 (1H, m), 2.28 (1H, m), 2.45 (1H, m), 2.90–3.10 (3H, m), 3.40 (1H, m), 3.70 (2H, m), 3.85 (1H, m), 4.12 (1H, m), 4.30 (1H, m), 4.46 (1H, m), 4.56 (1H, m), 7.20–7.35 (5H, m). Anal. Calc'd. for C$_{44}$H$_{68}$O$_8$N$_6$S$_2$% C, 43.38 H, 5.34; N, 5.63 Found % C, 43.04; H, 4.94; N, 5.92 Includes 3.05 H$_2$O and 4.95 TFA

Example 22

Disulphide of 2(S)-[2(S)-[2(R)-Amino-3-mercapto]propylamino-3(S)-methyl]pentyloxy-3-phenylpropionyl-homoserine To a solution of 2(S)-[2(S)-[2(R)-Amino-3-mercapto]propylamino-3(S)-methyl]pentyloxy-3-phenylpropionyl-homoserine lactone (87.8 mg 0.122 mmol) in methanol (12.2 ml), was added iodine, (28.7 mg, 0.131 mmol), after 15 minutes of the crude reaction mixture (8.2 ml) was treated with 1M sodium hydroxide (0.409 ml) and after 30 minutes was purified directly by HPLC using a gradient elution 95:5 to 5:95% water:acetonitrile containing 0.1% trifluoroacetic acid, to afford the title compound. NMR ($d_6$DMSO) δ0.70 (3H, d, J=6.8 Hz), 0.82 (3H, t, J=7.0 Hz), 1.10 (1H, m), 1.38 (1H, m), 1.70–2.00 (2H, m), 2.70–3.80 (13H, m), 4.02 (1H, m), 4.36 (1H, m), 7.20–7.40 (5H, m). Anal. Calc'd. for $C_{44}H_{72}O_{10}N_6S_2$% C, 43.38 H, 5.48; N, 5.68 Found % C, 43.39; H, 5.47; N, 5.75 Includes 1.85 $H_2O$ and 4.7 TFA

Example 23

Disulphide of 2(S)-[2(S)-[2(R)-Amino-3-mercapto]propylamino-3(S)-methyl]pentyloxy-3-methylbutanoyl-methionine methyl ester To a solution of 2(S)-[2(S)-[2(R)-Amino-3-mercapto]propylamino-3(S)-methyl]pentyloxy-3-methylbutanoyl-methionine methyl ester (38 mg 0.053 mmol) in methanol (7 ml), was added iodine, (11.4 mg, 0.045 mmol) after 15 minutes of the crude reaction mixture was purified directly by HPLC using a gradient elution 95:5 to 5:95% water:acetonitrile containing 0.1% trifluoroacetic acid, to afford the title compound. NMR($CD_3OD$) δ0.90–1.10 (12H, m), 1.30 (1H, m), 1.60 (1H, m), 1.90 (1H, m), 1.90–2.10 (2H, m), 2.10 (3H, s), 2.17 (1H, m), 2.40–2.70 (2H, m), 3.00–3.10 (2H, m), 3.20–3.35 (2H, m), 3.50 (1H, m), 3.65 (1H, m), 3.73 (3H, m), 3.90 (1H, m), 4.72 (1H, dd, J=4.5 and 9.7 Hz).

Anal. Calc'd. for $C_{40}H_{80}O_8N_6S_2$% C, 39.43 H, 5.67; N, 5.39 Found % C, 39.42; H, 5.66; N, 5.52 Includes 1.1 $H_2O$ and 5.6 TFA

Example 24

In vitro inhibition of ras farnesyl transferase

The assay was conducted as described in Pompliano, et. al., Biochemistry 31, 3800 (1992) with the exception of utilizing recombinant human farnesyl transferase in place of the partially purified bovine enzyme described therein. The activity of the compounds of this invention is shown in Table 1.

TABLE 1

Inhibition of RAS farnesylation by compounds of this invention

| Compound | $IC_{50}$ (nM)* |
|---|---|
| 2(S)-[2(S)-[2(R)-Amino-3-mercapto]propyl-amino-3(S)-methyl]-pentyloxy-3-phenyl-propionyl-homoserine | 5 |
| 2(S)-[2(S)-[2(R)-Amino-3-mercapto]propyl-amino-3(S)-methyl]-pentyloxy-2-methyl-3-phenylpropionyl-homoserine | 7 |
| 2(S)-[2(S)-[2(R)-Amino-3-mercapto]propyl-amino-3(S)-methyl]-pentyloxy-4-pentanoyl-homoserine | 18 |
| 2(S)-[2(S)-[2(R)-Amino-3-mercapto]propyl-amino-3(S)-methyl]-pentyloxypentanoyl-homoserine | 7 |
| 2(S)-[2(S)-[2(R)-Amino-3-mercapto]propyl-amino-3(S)-methyl]-pentyloxy-4-methyl-pentanoyl-homoserine | 19 |
| 2(S)-[2(S)-[2(R)-Amino-3-mercapto]propyl-amino-3(S)-methyl]-pentyloxy-3-methyl-butanoyl-homoserine | 1.4 |

TABLE 1-continued

Inhibition of RAS farnesylation by compounds of this invention

| Compound | $IC_{50}$ (nM)* |
|---|---|
| 2(S)-[(S)-[2(R)-amino-3-mercapto]propyl-amino-3(S)-methyl]-pentyloxy-3-phenyl-butanoyl-homoserine | 17 |
| 2(S)-[2(S)-[2(R)-Amino-3-mercapto]propyl-amino-3(S)-methyl]-pentylthio-2-methyl-3-phenylpropionyl-homoserine | 240 |
| 2(S)-[2(S)-[2(R)-Amino-3-mercapto]propyl-amino-3(S)-methyl]-pentylsulfonyl-2-methyl-3-phenylpropionyl-homoserine | 980 |
| 2(S)-[2(S)-[2(R)-Amino-3-mercapto]propyl-amino-3(S)-methyl]-pentyloxy-3-phenyl-propionyl-methionine | 4 |
| 2(S)-[2(S)-[2(R)-Amino-3-mercapto]propyl-amino-3(S)-methyl]-pentyloxy-3-phenyl-propionyl-methionine sulfone | 2.2 |

*$IC_{50}$ is the concentration of the test compound which gives 50% inhibition of FTase under the described assay conditions.

Example 25

In vivo ras farnesylation assay

The cell line used in this assay was the v-ras line, which expressed viral Ha-ms p21. The assay was performed essentially as described in DeClue, J. E. et. al., Cancer Research 51, 712–717, (1991). Cells in 10 cm dishes at 50–75% confluency were treated with the test compound (final concentration of solvent, methanol or dimethyl sulfoxide, was 0.1%). After 4 hours at 37° C., the cells were labelled in 3 ml methionine-free DMEM supplemented with 10% regular DMEM, 2% fetal bovine serum and 400 μCi[$^{35}$S]methionine (1000 Ci/mmol). After an additional 20 hours, the cells were lysed in 1 ml lysis buffer (1% NP40/20 mM HEPES, pH 7.5/5 mM $Mg/Cl_2$/1mM DTT/10 μg/ml aprotinen/2 μg/ml leupeptin/2 μg/ml antipain/0.5 mM PMSF) and the lysates cleared by centrifugation at 100,000×g for 45 minutes. Aliquots of lysates containing equal numbers of acid-precipitable counts were bought to 1 ml with IP buffer (lysis buffer lacking DTT) and immunoprecipitated with the ras-specific monoclonal antibody Y13-259 (Furth, M. E. et. al., J. Virol. 43, 294–304, (1982)). Following a 2 hour antibody incubation at 4° C., 200 μl of a 25% suspension of protein A-Sepharose coated with rabbit anti rat IgG was added for 45 minutes. The immunoprecipitates were washed four times with IP was buffer (20 nM HEPES, pH 7.5/1 mN EDTA/1% Triton X-100.0.5% deoxycholate/0.1%/SDS.0.1M NaCl) boiled in SDS-Page sample buffer and loaded on 13% acrylamide gels. When the dye front reached the bottom, the gel was fixed, soaked in Enlightening, dried and autoradiographed. The intensities of the bands corresponding to farnesylated and nonfarnesylated ras proteins were compared to determine the percent inhibition of farnesyl transfer to protein. Data for representative test compounds are tabulated in Table 2.

TABLE 2

Inhibition of RAS farnesylation by compounds of this invention in the v-ras cell line

| Compound | $IC_{50}$ (μM) |
|---|---|
| 2(S)-[2(S)-[2(R)-Amino-3-mercapto]propyl-amino-3(S)-methyl]-pentyloxy-3-phenyl-propionyl-homoserine lactone | 2.5 |

TABLE 2-continued

Inhibition of RAS farnesylation by compounds of this invention in the v-ras cell line

| Compound | IC$_{50}$ (µM) |
|---|---|
| 2(S)-[2(S)-[2(R)-Amino-3-mercapto]propyl-amino-3(S)-methyl]-pentyloxy-2-methyl-3-phenylpropionyl-homoserine lactone | 50 |
| 2(S)-[2(S)-[2(R)-Amino-3-mercapto]propyl-amino-3(S)-methyl]-pentyloxy-4-pentanoyl-homoserine lactone | 10 |
| 2(S)-[2(S)-[2(R)-Amino-3-mercapto]propyl-amino-3(S)-methyl]-pentyloxypentanoyl-homoserine lactone | 10 |
| 2(S)-[2(S)-[2(R)-Amino-3-mercapto]propyl-amino-3(S)-methyl]-pentyloxy-4-methyl-pentanoyl-homoserine lactone | 10 |
| 2(S)-[2(S)-[2(R)-Amino-3-mercapto]propyl-amino-3(S)-methyl]-pentyloxy-3-phenyl-propionyl-methionine methyl ester | 0.1 |
| 2(S)-[2(S)-[2(R)-Amino-3-mercapto]propyl-amino-3(S)-methyl]-pentyloxy-3-phenyl-propionyl-methionine sulfone methyl ester | 0.1 |
| 2(S)-[2(S)-[2(R)-Amino-3-mercapto]-propyl-amino-3(S)-methyl]-pentyloxy)-3-phenylpropionyl-methionine sulfone isopropyl ester | 0.1 |

What is claimed is:

1. A compound which inhibits farnesyl-protein transferase of the formula III:

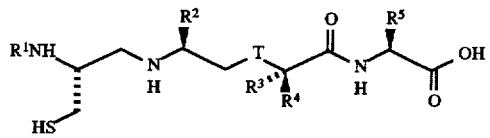

wherein:

R$^1$ is hydrogen, an alkyl group, an aralkyl group an acyl group, an aracyl group, an aroyl group, an alkylsulfonyl group, aralkylsulfonyl group or arylsulfonyl group, wherein alkyl and acyl groups comprise a straight chain or branched chain hydrocarbons of 1 to 6 carbon atoms;

R$^2$, R$^3$ and R$^5$ are independently selected from
  a) a side chain of naturally occurring amino acids;
  b) a side chain of oxidized forms of naturally occurring amino acids which comprise:
    i) methionine sulfoxide or
    ii) methionine sulfone; or
  c) a substituted or unsubstituted aliphatic, aromatic or heteroaromatic group, which comprises allyl, cyclohexyl, phenyl, pyridyl, imidazolyl or branched or unbranched saturated chains of 2 to 8 carbon atoms, wherein the substituted aliphatic group is substituted with an aromatic or heteroaromatic ring;

R$^4$ is hydrogen or an alkyl group, wherein the alkyl group comprises straight chain or branched chain hydrocarbons of 1 to 6 carbon atoms;

T is O or S(O)$_m$;
m is 0, 1 or 2;

or the pharmaceutically acceptable salts thereof.

2. The compound of claim 1 which is:

2(S)-[2(S)-[2(R)-Amino-3-mercapto]propylamino-3(S)-methyl]pentyloxy-3-phenylpropionyl-methionine

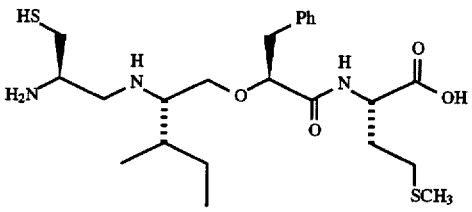

or the pharmaceutically acceptable salts thereof.

3. The compound of claim 1 which is: 2(S)-[2(S)-[2(R)-Amino-3-mercapto]propylamino-3(S)-methyl]pentyloxy-3-phenylpropionyl-methionine sulfone

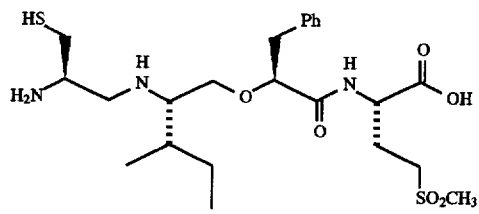

or the pharmaceutically acceptable salts thereof.

4. A pharmaceutical composition comprising a pharmaceutical carrier, and dispersed therein, a therapeutically effective amount of a compound of claim 1.

5. A compound which inhibits farnesyl-protein transferase which is:

2(S)-[2(S)-[2(R)-Amino-3-mercapto]propylamino-3(S)-methyl]-pentyloxy-3-phenylpropionyl-methionine, 2(S)-[2(S)-[2(R)-Amino-3-mercapto]propylamino-3(S)-methyl]-pentyloxy-3-phenylpropionyl-methionine sulfone, 2(S)-[2(S)-[2(R)-Amino-3-mercapto]propylamino-3(S)-methyl]-pentyloxy-3-phenylpropionyl-methionine sulfone, 2(S)-[2(S)-[2(R)-Amino-3-mercapto]propylamino-3(S)-methyl]pentyloxy-3-naphth-2-yl-propionyl-methionine sulfone, 2(S)-[2(S)-[2(R)-Amino-3-mercapto]propylamino-3(S)-methyl]pentyloxy-3-naphth-1-yl-propionyl-methionine sulfone, or 2(S)-[2(S)-[2(R)-Amino-3-mercapto]propylamino-3(S)-methyl]pentyloxy-3-methylbutanoyl-methionine, or the pharmaceutically acceptable salts thereof.

6. A pharmaceutical composition comprising a pharmaceutical carrier, and dispersed therein, a therapeutically effective amount of a compound of claim 5.

* * * * *